US010351608B2

(12) United States Patent
Riser

(10) Patent No.: US 10,351,608 B2
(45) Date of Patent: *Jul. 16, 2019

(54) CCN3 AND CCN3 PEPTIDES AND ANALOGS THEREOF FOR THERAPEUTIC USE

(71) Applicant: Rosalind Franklin University of Medicine and Science, North Chicago, IL (US)

(72) Inventor: Bruce L. Riser, Kenosha, WI (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 99 days.

This patent is subject to a terminal disclaimer.

(21) Appl. No.: 14/821,494

(22) Filed: Aug. 7, 2015

(65) Prior Publication Data

US 2015/0337020 A1    Nov. 26, 2015

Related U.S. Application Data

(60) Division of application No. 13/725,658, filed on Dec. 21, 2012, now Pat. No. 9,114,112, which is a continuation-in-part of application No. 13/079,693, filed on Apr. 4, 2011, now Pat. No. 8,518,395.

(60) Provisional application No. 61/341,694, filed on Apr. 2, 2010.

(51) Int. Cl.
| | |
|---|---|
| *C07K 14/47* | (2006.01) |
| *A61K 38/17* | (2006.01) |
| *A61K 38/04* | (2006.01) |
| *A61K 9/00* | (2006.01) |
| *A61K 35/12* | (2015.01) |
| *A61K 38/10* | (2006.01) |
| *C07K 14/475* | (2006.01) |
| *A61K 35/28* | (2015.01) |
| *A61K 35/51* | (2015.01) |

(52) U.S. Cl.
CPC ............ *C07K 14/47* (2013.01); *A61K 9/0014* (2013.01); *A61K 35/12* (2013.01); *A61K 35/28* (2013.01); *A61K 35/51* (2013.01); *A61K 38/04* (2013.01); *A61K 38/10* (2013.01); *A61K 38/1709* (2013.01); *C07K 14/475* (2013.01); *C07K 14/4743* (2013.01)

(58) Field of Classification Search
None
See application file for complete search history.

(56) References Cited

U.S. PATENT DOCUMENTS

| | | |
|---|---|---|
| 7,780,949 B2 | 8/2010 | Riser |
| 8,518,395 B2 | 8/2013 | Riser |
| 9,114,112 B2 * | 8/2015 | Riser ................. A61K 38/1709 |
| 2003/0059768 A1 | 3/2003 | Vernet et al. |
| 2004/0009940 A1 | 1/2004 | Coleman et al. |
| 2004/0191230 A1 | 9/2004 | Auclair et al. |
| 2004/0224360 A1 | 11/2004 | Riser et al. |
| 2006/0004101 A1 * | 1/2006 | Okita .................... A23L 1/3051 514/561 |
| 2006/0178332 A1 | 8/2006 | Riser |
| 2007/0059314 A1 | 3/2007 | Plouet et al. |
| 2010/0004169 A1 | 1/2010 | Irvine et al. |

FOREIGN PATENT DOCUMENTS

| | | | |
|---|---|---|---|
| EP | 1382347 | | 1/2004 |
| WO | 204090109 A2 | | 10/2004 |
| WO | 2006036962 | | 4/2006 |
| WO | WO2006036962 | * | 4/2006 |
| WO | 2006074452 A2 | | 7/2006 |
| WO | WO2006074452 | * | 7/2006 |

OTHER PUBLICATIONS

Liu et al, Nephroblastoma overexpressed gene (NOV) codes for a growth factor that induces protein tyrosine phosphorylation, Gene 238 (1999) 471-478.*
Leask et al (J. Cell Commun. Signal. (2009) 3:89-94).*
Canadian liver foundation (download online from URL:<http://www.liver.ca/livewell/issues/2010_issue_spring_Issues_liver_cancer.aspx>).*
Dongiovanni et al (Current Pharmaceutical Design, 2013, 19, 5219-5238).*
Bataller et al (J. Clin. Invest. 115:209-218 (2005)).*
Akchurin et al. (Blood Purif 2015;39:84-92).*
Vetelainen et al. (Ann Surg. Jan. 2007;245(1):20-30) (Year: 2007).*
Gressner, O., et al.; "Connective tissue growt factor (CCN2, CTGF) and organ fibrosis: lessons from transgenic animals"; Liver International; first published online: Aug. 6, 2008; 1478-3231.
Wang, X., et al. "Adverse effects of high glucose and free fatty acid on cardiomyocytes are mediated by connective tissue growth factor." American Journal of Physiology—Cell Physiology 297.6 (2009): C1490-C1500.
Daniels, A., et al.; "Connective tissue growth factor and cardiac fibrosis"; Acta Physiologica, Article first published online: Nov. 27, 2008, 1748-1716.
Perbal, B.; "NOV and the CCN family of genes: structural and functional issues"; J. Clin. Pathol.: Molecular Pathology; 54: 57-79; 2001.
Schellenberger, et al.; "A recombinant polypeptide extends the in vivo half-life of peptides and proteins in a tunable manner"; Nature Biotechnology, vol. 27, No. 12; Dec. 2009.
Le Guillou; download on Apr. 1, 2014 from URL: <https://www.alainleguillou.com/medical-information>.

(Continued)

*Primary Examiner* — Sergio Coffa
(74) *Attorney, Agent, or Firm* — Joseph A. Fuchs; Greensfelder, Hemker & Gale, P.C.

(57) ABSTRACT

The present invention provides a method for treating a human patient with a pathology by administering to the subject an effective amount of an agent selected from the group of: native full-length CCN3 proteins; analog CCN3 full-length proteins with native cysteine residues substituted by a replacement amino acid; CCNp native peptide fragments having from about 12 to about 20 amino acids; analog CCNp peptide fragments with native cysteine residues substituted with a replacement amino acid; and combinations thereof.

13 Claims, 23 Drawing Sheets

Specification includes a Sequence Listing.

(56) References Cited

OTHER PUBLICATIONS

Leslie; Science Now; May 2012; retrieved on Oct. 22, 2013 from URL: <http://news.sciencemag.org/health/2012/05/tumor-blocker-may-fight-fibrosis>.
Panos, et al.; "Clinical deterioration in patients with idiopathic pulmonary fibrosis: causes and assessment"; Am. J. Med. 1990; April; 88(4): 396-404.
Kular, et al.; "NOV/CCN3 Attenuates Inflammatory Pain Through Regulation of Matrix Matelloproteinases-2 and -9"; J. of Neuroinflammation; 2012; http://www.jneuroinflammation.com/content/9/1/36.
Ghosh, et al.; "PAI-1 in Tissue Fibrosis"; J. of Cellular Physiology; pp. 493-507; Feinberg Cardiovascular Research Institute, Feinberg School of Medicine, Northwestern University, Published online in wileyonlinelibrary.com, Apr. 4, 2011.
McIntosh, et al.; "Selective CCR2-Targeted Macrophage Depletion Ameliorates Experimental Mesangioproliferative Glomerylonephritis"; Clinical and Experimental Immunology; 155:295-303; British Society for Immunolog. and Oprey Pharmaceuticals.
Tsoutsman, et al.; "Severe Heart Failure and Early Mortality in a Double-Maturation Mouse Model of Familial Hypertrophic Cardiomyopathy"; 2008 American Heart Association, Inc.; pp. 1820-1831; http://circ.ahajournals.org.
Cozzolino, et al.; "CCN2 (CTGF) Gene Polymorphism is a Novel Prognostic Risk Factor for Cardiovascular Outcomes in Hemodialysis Patients"; Blood Purification; Nov. 11, 2010; www.karger.com/bpu.
Brigstock, D. R.; "Regulation of angiogenesis and endothelial cell function by connective tissue growth factor and cysteine-rich 61 (CYR61)"; Angiogenesis; 5:153-165; 2002.
Bradham, MD, et al.; "Connective tissue growth factor: a cysteine-rich mitogen secreted by human vascular endothelial cells is related to SCR-induced immediate early gene product CEF-10"; J. of Cell. Biolog.; 114:1285-1294; 1991.
Tsai, et al.; "Expression and function of CYR61, an angiogenic factor, in breast cancer cell lines and tumor biopsies"; Cancer Research; 60:5603-5607; 2000.
Tsai, et al.; "Expression and regulation of CYR61 in human breast cancer cell lines"; Oncogene 21:964-973, 2002.
Sampath et al.; "CYR61, a member of the CCN family, is required for MCF-7 cell proliferation: regulation by 17 beta-estradiol and overexpression in human breast cancer"; Endocrinology 142:2540-2548, 2001.
Sampath et al.; "Aberrant expression of CYR61, a member of the CCN family (i.e. CCN1), and dysregulation by 17 beta-estradiol and basic fibroblast growth factor in human uterine leiomyomas." Journal of Clinical Endocrinology and Metabolism, 86: 1707-1715, 2001.
Sampath et al.; "The angiogenic factor CYR61 is induced by progestin R5020 and is necessary for mammary adenocarcinorma cell growth"; Endocrine, 18: 147-159, 2002.
Xie et al.; "Breast cancer, CYR61 is overexpressed, estrogen-inducible, and associated with more advanced disease"; Journal of Biological Chemistry, 276: 14187-14194, 2001.
Xie et al.; "Elevated levels of connective tissue growth factor, WISP-1, and CYR61 in primary breast cancers associated with more advanced features"; Cancer Research, 61: 8917-8923, 2001.
Rageh et al.; "Steroidal regulation of connective tissue growth factor (CCN2; CTGF) synthesis in the mouse uterus"; J Clin. Pathol:Molecular Pathology, 54: 338-346, 2001.
Cheon et al.; "A genomic approach to identify novel progesterone receptor regulated pathways in the uterus during implantation"; Molecular Endocrinology, 16: 2853-2871; 2002.
Wandji et al.; "Messenger ribonucleic acids for MAC25 and connective tissue growth factor (CTGF) are inversely regulated during folliculogenesis and early luteogenesis"; Endocrinology, 141:2648-2657; 2000.
Slee et al.; "Differentiation-dependent expression of connective tissue growth factor and lysyl oxidase messenger ribonucleic acids in rat granulose cells"; Endocrinology, 142: 1082-1089; 2001.
Harlow & Hillier; "Connective tissue growth factor in the ovarian paracrine system"; Molecular and Cellular Endocrinology, 187: 23-27; 2002.
Harlow et al.; "FSH and TGF-beta superfamily members regulate granulose cell connective tissue growth factor gene expression in vitro and in vivo"; Endocrinology, 143: 3316-3325; 2002.
Liu et al.; "Gonodotrophins inhibit the expression of insulin-like growth binding protein-related protein-2 mRNA in cultured human granulose-luteal cells"; Molecular Human Reproduction, 8:136-141; 2002.
Kyurkchiev, S. et al.; "Potential cellular conformations of the CCN3 (NOV) protein"; Cellular Communication and Signaling, 2: 9-18; 2004.
Li, C. L. et al.; "A role for CCN3 (NOV) in calcium signaling"; Journal of Clinical Pathology:Molecular Pathology, 55: 250-261; 2002.
Dean R.G., et al.; "Connective tissue growth factor and cardiac fibrosis after myocardial infarction"; Journal of Histochemistry & Cytochemistry. 53(10): 1245-56, 2005.
Shi-Wen, X., et al.; "Autocrine overexpression of CTGF maintains fibrosis: RDA analysis of fibrosis genes in systemic sclerosis"; Experimental Cell Research. 259(1):213-24, 2000.
Ozaki, S., et al.; "Diffuse expression of heparan sulfate proteoglycan and connective tissue growth factor in fibrous septa with many mast cells relate to unresolving hepatic fibrosis of congenital hepatic fibrosis"; Liver International. 25(4):817-28, 2005.
Sakamoto, N., et al.; "Influence of glucose and inflammatory cytokines on TGF-beta1 and CTGF mRNA expressions in human peritoneal mesothelial cells"; International Journal of Molecular Medicine. 15(6):907-11, 2005.
Zarrinkalam, K.H., et al.; "Connective tissue growth factor and its regulation in the peritoneal cavity of peritoneal dialysis patients"; Kidney International. 64(1):331-8, 2003.
Riser, B. L. et al.; "Urinary CCN2 (CTGF) as a possible predictor of diabetic nephropathy: Preliminary report"; Kidney International. 64: 451-458, 2003.
Wang, S., et al.; "Connective tissue growth factor in tubulointerstitial injury of diabetic nephropathy"; Kidney International. 60(1):96-105, 2001.
Perbal, B., J Cell Commun Signal, 2(1-2):3-7, Jun. 2008.
Yeger et al., J Cell Commun Signal, 1(3-4): 159-164, Dec. 2007.
Brigstock (2003). J. Endocrinology, 178, 169-175.
Jeager et al. (2002) Am. J. Neurorad. 23, 200-207.
Perbal (2003) Exert Rev Molec Diag. 3, 597-604.
Gupta et al.; "NOV(CCN3 Functions as a Regulator of Human Hematopoietic Stem of Progenitor Cells"; Science 2007, 316(5824):590-593; Abstract.
Uniprot-Direct Submission P48745 (Mar. 2, 2010) [Retrieved from Internet Jul. 7, 2011, <http://www. uniprot.org/uniprot/P487 4 5.txt?version-94>].
Brigstock, D. R.; "Regulation of angiogenesis and endothelial cell function by connective tissue growth factor (CTGF) and cysteine-rich 61 (CYR61)"; Angiogenesis 5: 153-165, 2002.
Mason, R.; "Connective tissue growth factor (CCN2), a pathogenic factor in diabetic nephropathy. What does it do? How does it do it?"; J. Cell Commun. Signal 3: 95-104, 2009.
Riser, B., et al.; "CCN3 is a negative regulator of CCN2 and a novel endogenous inhibitor of the fibrotic pathway in an in vitro model of renal disease"; American J Pathology, 174, 5, 2009.
McCallum, L., et al.; "CCN3: a key growth regulator in Chronic Myeloid Leukaemia"; J. Cell. Commun. Signal; Jun. 2009; 3(2): 115-124.
Bhagavathula, N., et al; "Fibroblast response to gadolinium: role for platelet-derived growth factor receptor." Invest Radiol 45(12): 769-777; 2010.
Riser, B., et al.; "Gadolinium-induced fibrosis is counter-regulated by CCN3 in human dermal fibroblasts: a model for potential treatment of nephrogenic systemic fibrosis." J Cell Commun Signal 6(2): 97-105; 2012.
Brigstock, D.; "Connective tissue growth factor (CCN2, CTGF) and organ fibrosis: lessons from transgenic animals"; J. Cell Commun.

(56) References Cited

OTHER PUBLICATIONS

Signal.; (2010) 4:1-4—Springer; DOI 10.1007/s12079-009-0071-5; published online Oct. 2, 2009.

* cited by examiner

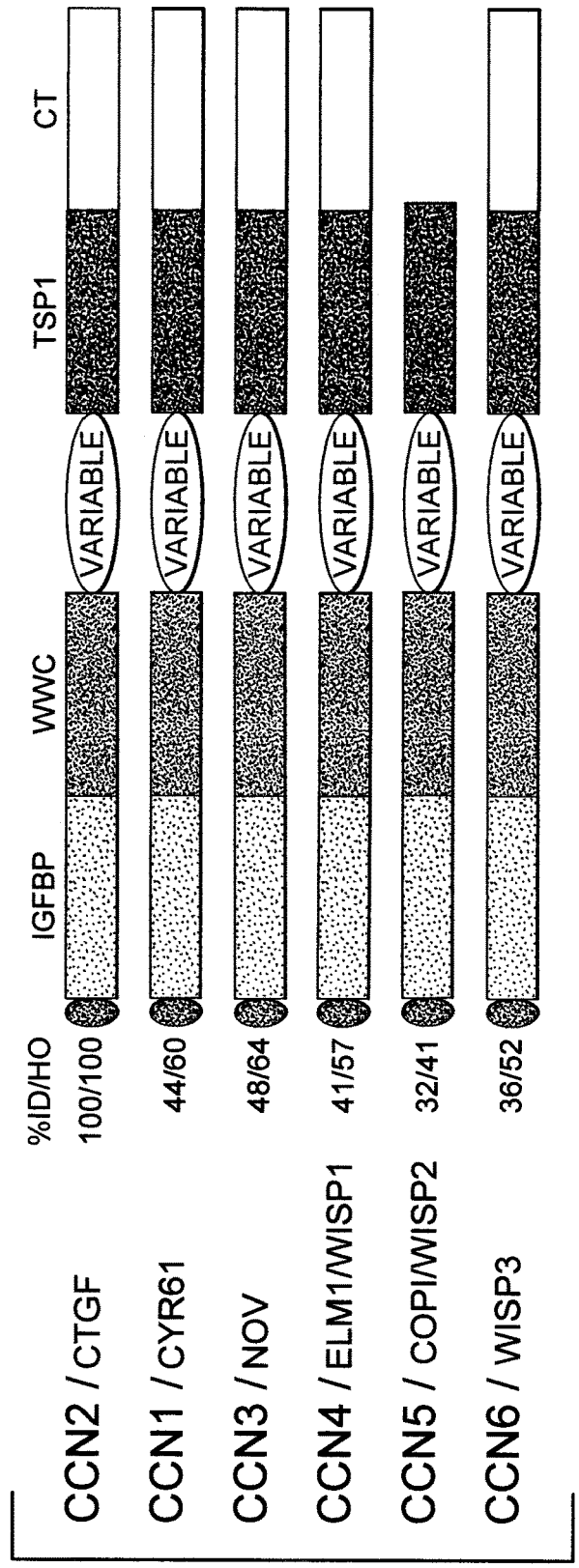

FIG. 2

ORIGINAL SEQUENCE - MOUSE CCN3 (NOV)

MSLFLRKRCLCLGFLLFHLLSQVSASLRCPSRCPPKCPSISPTCAPGVRSVLDGCSCCP
VCARQRGESCSEMRPCDQSSGLYCDRSADPNNQTGICMVPEGDNCVFDGVIYRNGEKFE
PNCQYFCTCRDGQIGCLPRCQLDVLLPGPDCPAPRKVAVPGECCEKWTCGSDEQGTQGT
LGGLALPAYRPEATVGVEVSDSSINCIEQTTEWSACSKSCGMGVSTRVTNRNRQCEMVK
QTRLCIVRPCEQEPEEVTDKKGKKCLRTKKSLKAIHLQFENCTSLYTYKPRFCGVCSDG
RCCTPHNTKTIQVEFQCLPGEIIKKPVMVIGTCTCYSNCPQNNEAFLQDLELKTSRGEI

MODIFIED SEQUENCE USED TO DESIGN PEPTIDES - SERINE
REPLACEMENT OF CYSTEINE

MSLFLKRSLSLGFLLFHLLSQVSASLRSPSRSPPKSPSISPTSAPGVRSVLDGSSSSP
VSARQRGESSSEMRPSDQSSGLYSDRSADPNNQTGISMVPEGDNSVFDGVIYRNGEKFE
PNSQYFSTSRDGQIGSLPRSQLDVLLPGPDSPAPRKVAVPGESSEKWTSGSDEQGTQGT
LGGLALPAYRPEATVGVEVSDSSINSIEQTTEWSASSKSSGMGVSTRVTNRNRQSEMVK
QTRLSIVRPSEQEPEEVTDKKGKKSLRTKKSLKAIHLQFENSTSLYTYKPRFSGVSSDG
RSSTPHNTKTIQVEFQSLPGEIIKKPVMVIGTSTSYSNSPQNNEAFLQDLELKTSRGEI

FIG. 3

| | | | |
|---|---|---|---|
| MSLFLRKRSLSLGFL | 1 | WSASSKSSGMGVSTR | 22 |
| SLGFLLFHLLSQVSA | 2 | GVSTRVTNRNRQSEM | 23 |
| SQVSASLRSPSRSPP | 3 | RQSEMVKQTRLSIVR | 24 |
| RSPSRSPPKSPSISPTSA | 4 | LSIVRPSEQEPEEVT | 25 |
| SPTSAPGVRSVLDGS | 5 | PEEVTDKKGKKSLRT | 26 |
| VLDGSSSPVSARQR | 6 | KSLRTKKSLKAIHLQ | 27 |
| SARQRGESSSEMRPS | 7 | AIHLQFENSTSLYTY | 28 |
| EMRPSDQSSGLYSDR | 8 | SLYTYKPRFSGVSSD | 29 |
| LYSDRSADPNNQTGI | 9 | GVSSDGRSSTPHNTK | 30 |
| NQTGISMVPEGDNSV | 10 | PHNTKTIQVEFQSLP | 31 |
| GDNSVFDGVIYRNGE | 11 | FQSLPGEIIKKPVMV | 32 |
| YRNGEKFEPNSQYF | 12 | KPVMVIGTSTSYSNS | 33 |
| SQYFSTSRDGQIGSL | 13 | SNSPQNNEAFLQDL | 34 |
| QIGSLPRSQLDVLLP | 14 | AFLQDLELKTSRGEI | 35 |
| DVLLPGPDSPAPRKV | 15 | KQTRLSIVRPSEQ 36 | (PART OF #23) |
| APRKVAVPGESSEK | 16 | FSGVSSDGRSSTPH 37 | (PART OF #29 AND #30) |
| SSEKWTSGSDEQGTQGT | 17 | SDRSADPNNQTGIS 38 | (PART OF #8 AND #9) |
| DEQGTQGTLGGLALP | 18 | QTTEW SASSKSSGMG 39 | (PART OF #s 20,21,22) |
| LALPAYRPEATVGV | 19 | SSKSSGMGVSTRVTN 40 | (PART OF #s 20,21,22) |
| ATVGVEVSDSSINSI | 20 | | |
| SINSIEQTTEWSASS | 21 | | |

FIG. 5

```
MSLFLRKRSLSLGFLLFHLLSQVSASLRSPSRSPPKSPSISPTSAPGVRSVLDGSSSSP
VSARQRGESSSEMRPSDQSSGLYSDRSADPNNQTGISMVPEGDNSVFDGVIYRNGEKFE
PNSQYFSTSRDGQIGSLPRSQLDVLLPGPDSPAPRKVAVPGESSEKWTSGSDEQGTQGT
LGGLALPAYRPEATVGVEVSDSSINSIEQTTEWSASSKSSGMGVSTRVTNRNRQSEMVK
QTRLSIVRPSEQEPEEVTDKKGKKSLRTKKSLKAIHLQFENSTSLYTYKPRFSGVSSDG
RSSTPHNTKTIQVEFQSLPGEIIKKPVMVIGTSYSNSPQNNEAFLQDLELKTSRGEI
```

SHOWS REGIONS ON THE CCN3 SEQUENCE CHOSEN- ALL CYSTEINES WERE REPLACED BY SERINES (AS SHOWN). DOTTED LINE SHOWS OVERLAPPING PEPTIDES MADE. BOLDED SHOWS SEQUENCE OF PEPTIDES DESIGNED FOR SPECIFIC REGIONS, ALSO OVERLAPPING WITH OTHERS MADE.

FIG. 6

FROM THE THROMBOSPONDIN LIKE (TSP) ELEMENT OF MOUSE CCN3:

(CCN3p 39) QTTEWSACSKSCGM   APPROX 90% HOMOLOGY, SEQUENCE APPROX 206-220

(CCN3p 40) CSKSCGMGVSTRVTN   APPROX 90% HOMOLOGY, SEQUENCE APPROX 213-227

(CCN3p 36) KQTRLCIVRPCEQ   APPROX 50% HOMOLOGY, SEQUENCE APPROX 236-248

FROM THE C-TERM ELEMENT, MOUSE CCN3:

(CCN3p 37) FCGVCSDGRCCTPH   APPROX 92.9% HOMOLOGY, SEQUENCE APPROX 289-302

FROM INSULIN-LIKE GROWTH FACTOR BINDING DOMAIN (IGFBD) ELEMENT, MOUSE CCN3:

(CCN3p 38) CDRSADPNNQTGIC   APPROX 28% HOMOLOGY, SEQUENCE APPROX 84-98

FIG. 7A

PEPTIDES MADE AND TESTED: (WITH ANY CYSTEINES [C] FOUND IN THE NATURAL SEQUENCE REPLACED WITH SERINES [S])

CCN3p37    ACETYL-FSGVSSDGRSSTPH-NH2
CCN3p38    ACETYL-SDRSADPNNQTGIS-NH2

FIG. 7B

EQUIVALENT NATURAL SEQUENCE: (i.e. WITH CYSTEINES)

CCN3p37    (HUMAN & MOUSE)    FCGVCSDGRCCTPH    (IS THE SAME IN MOUSE AND HUMANS)
CCN3p38    (MOUSE)            CDRSADPNNQTGIC
CCN3p38    (HUMAN)            CDRSADPSNQTGIC    (CCN3) HUMAN IS ONE AA DIFFERENT FROM MOUSE

* BOLDED LETTER (AA) INDICATES THAT THE SEQUENCE IS DIFFERENT IN THIS POSITION THAN THAT MADE AND TESTED.

FIG. 7C

NATURAL SEQUENCE HUMAN CCN2 AND CCN3 AT THE REGIONS SELECTED FOR CCN3p37 AND CCN3p38 W/ CYSTEINES INTACT

FCGVCTDGRCCTPH   CCN2 HUMAN (BOLDED SHOWING SEQUENCE DIFFERENCES WITH CCN3)
FCGVCSDGRCCTPH   CCN3p37 HUMAN W/ CYSTEINES INTACT

CDFGSPANRKIGVC   CCN2 HUMAN (BOLDED SHOWING SEQUENCE DIFFERENCES WITH CCN3)
CDRSADPSNQTGIC   CCN3p38 HUMAN W/ CYSTEINES INTACT

\* NOTE THE SEQUENCE FOR CCN2 IS OFTEN QUITE DIFFERENT FROM THAT OF CCN3 EVEN UNDER OPTIMAL ALIGNMENT.

FIG. 7D

NATURAL SEQUENCE MOUSE CCN2 AND CCN3 AT THE REGIONS SELECTED FOR CCN3p37 AND CCN3p38 W/ CYSTEINES INTACT

FCGVCTDGRCCTPH   CCN2 MOUSE (BOLDED SHOWING SEQUENCE DIFFERENCES WITH CCN3)
FCGVCSDGRCCTPH   CCN3p37 MOUSE W/ CYSTEINES INTACT (SAME AS ABOVE-HUMAN)

CDFGSPANRKIGVC   CCN2 MOUSE (BOLDED SHOWING SEQUENCE DIFFERENCES WITH CCN3)
CDRSADPNNQTGIC   CCN3 CCN3p38 MOUSE W/ CYSTEINES INTACT (1 AA DIFFERENT FROM ABOVE-HUMAN AT CCN3)

\* NOTE THE SEQUENCE FOR CCN2 IS OFTEN QUITE DIFFERENT FROM THAT OF CCN3 EVEN UNDER OPTIMAL ALIGNMENT.

FIG. 7E
- CNP-37-12 ( SEQ. ID. NO. 37)    FSG/VSS/DGR/SST/PH        analog--serine replacement
- CNP-37-13 (SEQ.ID NOS. 48 & 63)  FCG/VCS/DGR/CCT/PH        native sequence
- CNP-37-14 (SEQ. ID. NO. 54)      G/VSS/DGR/SST/PH          analog--serine replacement- short FC(s) on N-term)
- CNP-37-15 (SEQ. ID. NO. 55)      FSG/VSS/DGR/SST/          analog--serine- short PH on C-term FIG. 7F
- CNP-38-1  (SEQ ID 38)    SDR/SAD/PNN/QTG/IS      analog--mouse serine replacement
- CNP-38-2  (SEQ ID 49)    CDR/SAD/PNN/QTG/IC      native mouse sequence
- CNP-38-3  (SEQ ID 56)    SDR/SAD/PSN/QTG/IS      analog human--serine replacement
- CNP-38-4  (SEQ ID 50)    CDR/SAD/PSN/QTG/IC      native human
- CNP-38-5  (SEQ ID 53)    SDR/SAD/PNN/ETG/IS      analog rat-- serine replacement
- CNP-38-6  (SEQ ID 52)    CDR/SAD/PNN/ETG/IC      native rat
- CNP-38-7  (SEQ ID 59)    R/SAD/PNN/QTG/IS        analog mouse-minus CD (or SD) at N-term, 1 serine remains
- CNP-38-8  (SEQ ID 60)    R/SAD/PNN/ETG/IS        analog rat- minus CD (or SD) at N-term, 1 serine remains
- CNP-38-9  (SEQ ID 57)    R/SAD/PSN/QTG/IS        analog human- minus CD (or SD) at N-term, 1 serine repl remains
- CNP-38-10 (SEQ ID 58)    SDR/SAD/PSN/QTG/IS-T    analog human --serine replacement + T on C-term
- CNP-38-11 (SEQ ID 61)    SDR/SAD/PSN/ETG/IS-T    native human +T on C-term

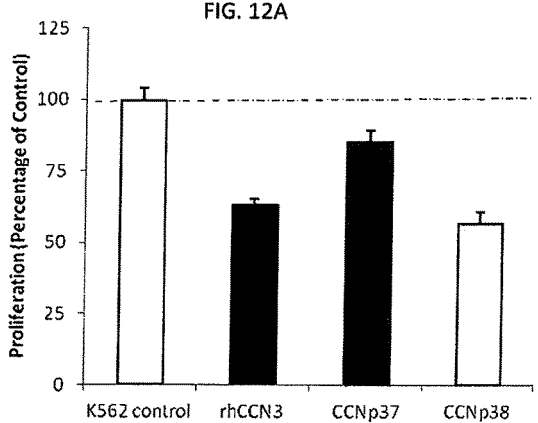

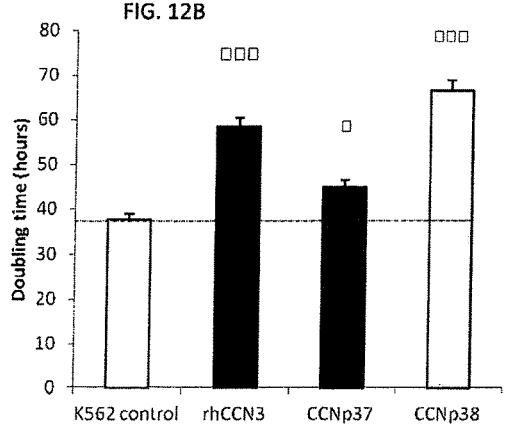

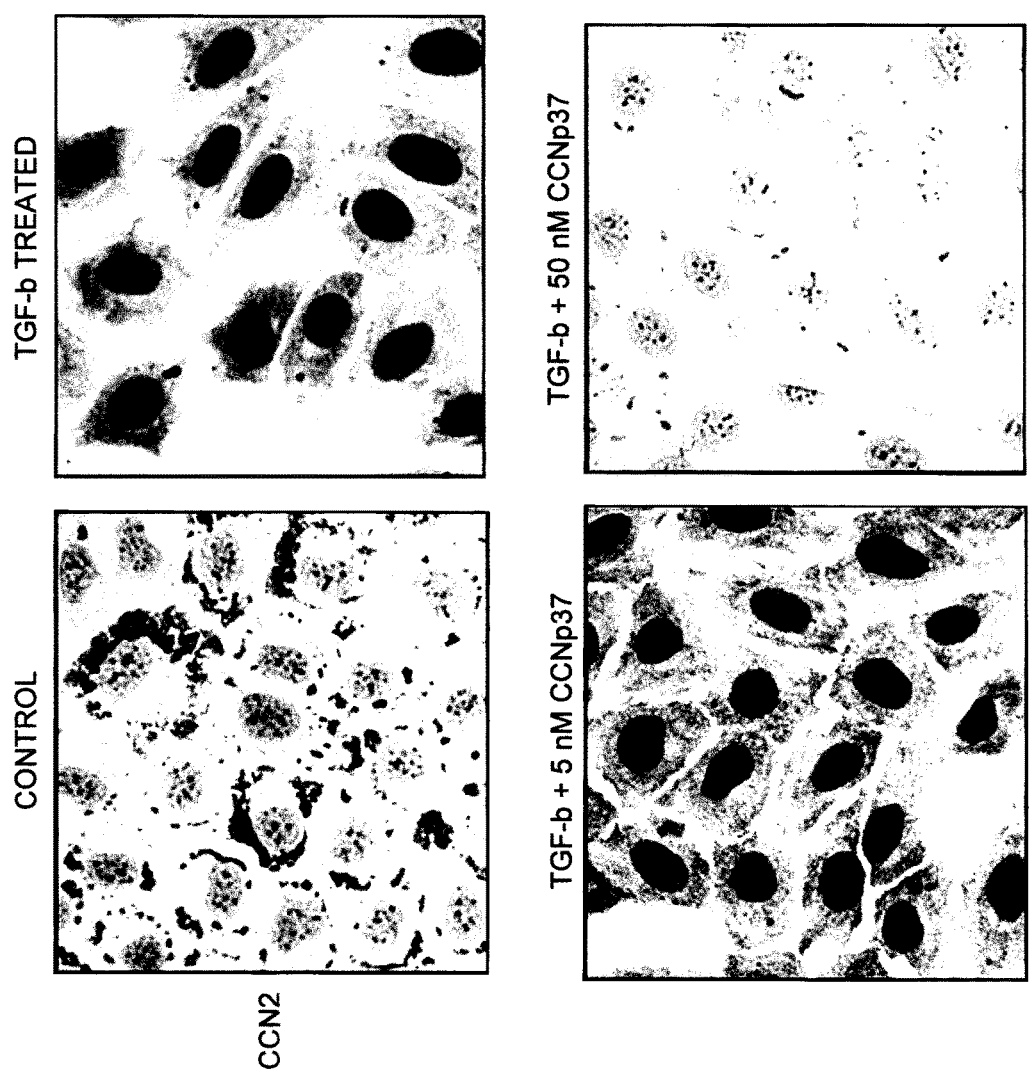

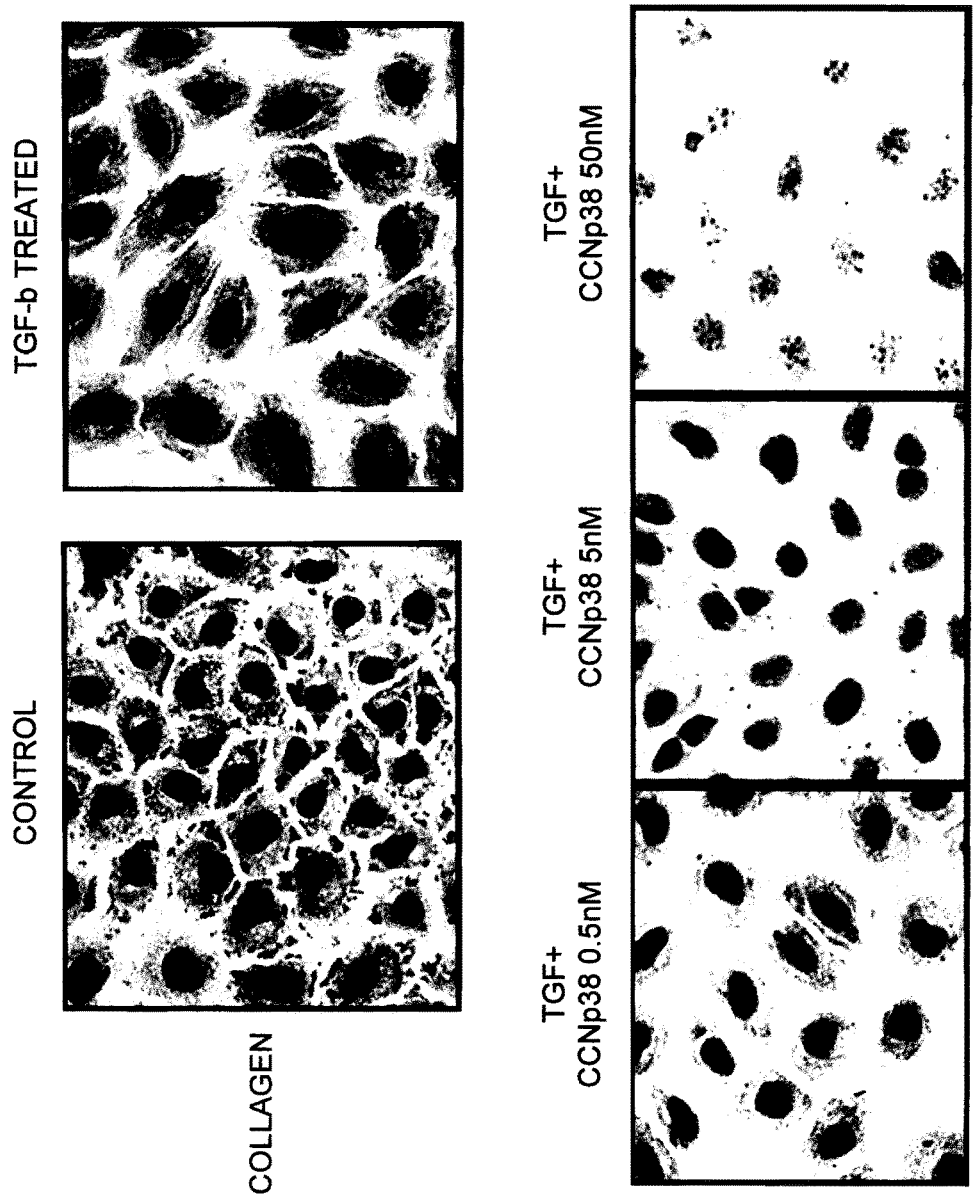

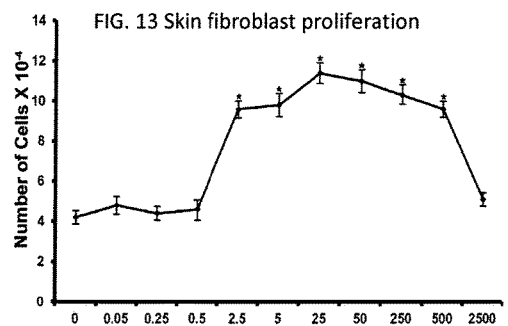
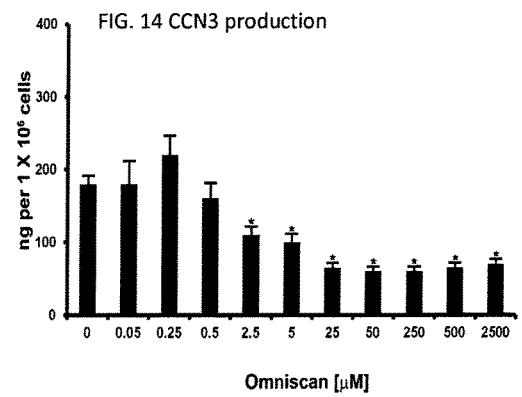
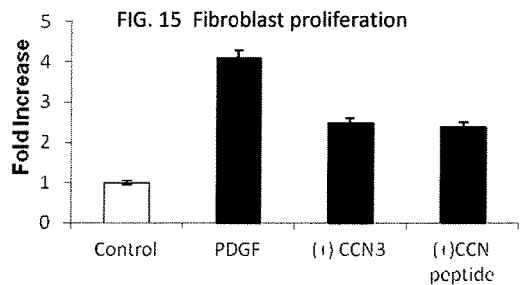
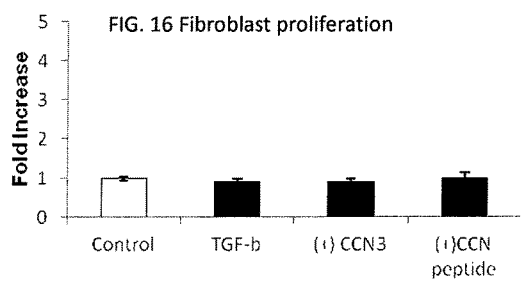
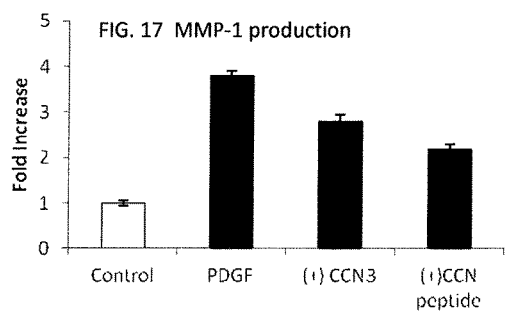
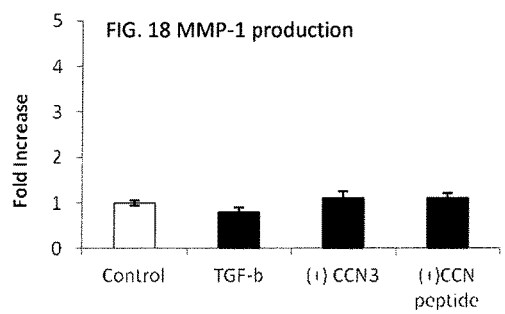
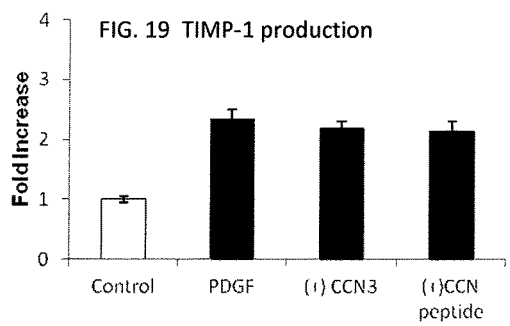
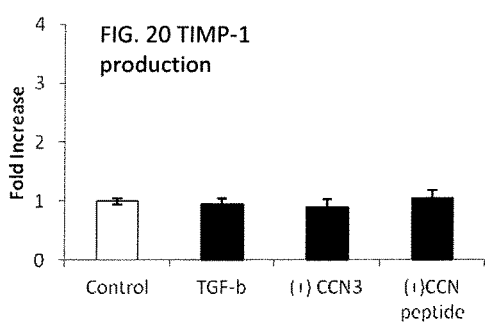

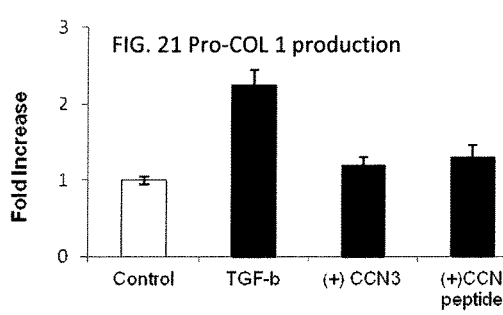

FIG. 21 Pro-COL 1 production

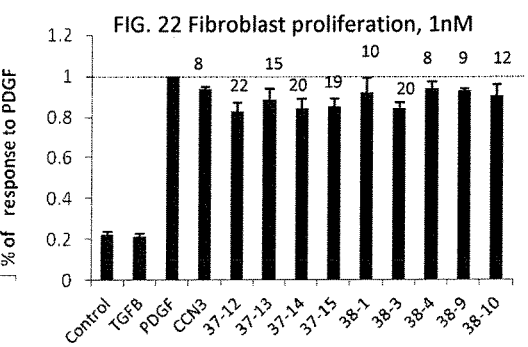

FIG. 22 Fibroblast proliferation, 1nM
Numbers above bars represent % decrease from PDGF control.

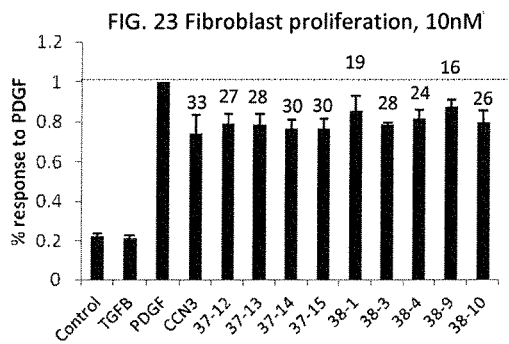

FIG. 23 Fibroblast proliferation, 10nM
Numbers above bars represent % decrease from PDGF control. Error bars are SE

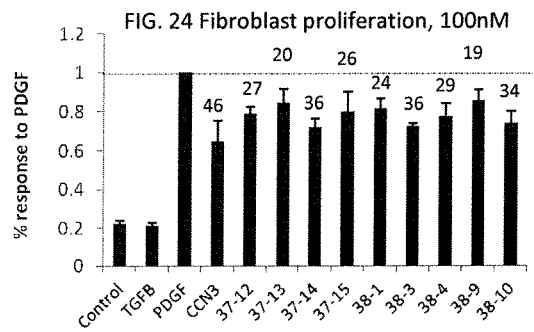

FIG. 24 Fibroblast proliferation, 100nM
Numbers above bars represent % decrease from PDGF control.

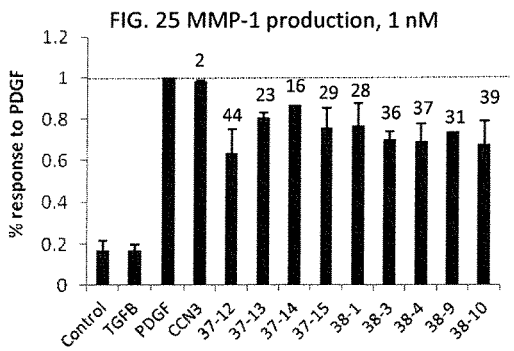

FIG. 25 MMP-1 production, 1 nM
Numbers above bars represent % decrease from PDGF control.

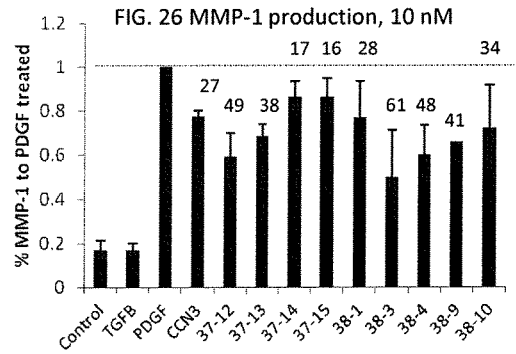

FIG. 26 MMP-1 production, 10 nM
Numbers above bars represent % decrease from PDGF control.

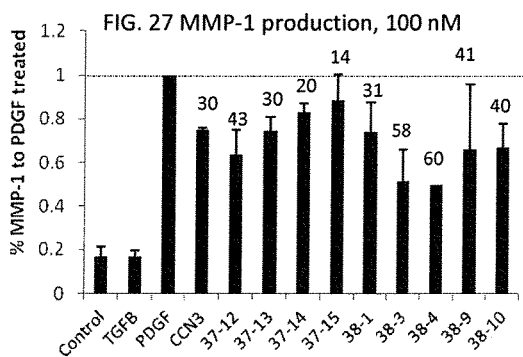

Numbers above bars represent % decrease from PDGF control.

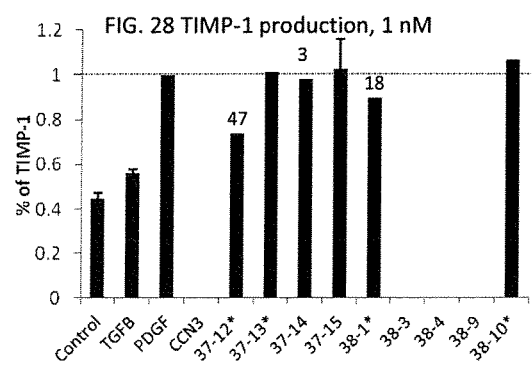

Vertical axis is % of TIMP-1 compared to TIMP-1 in PDGF group. Numbers above bar represent % decrease compared to PDGF group. . * denotes only 1 experiment preformed. Peptides with only 1 experiment have no SE.

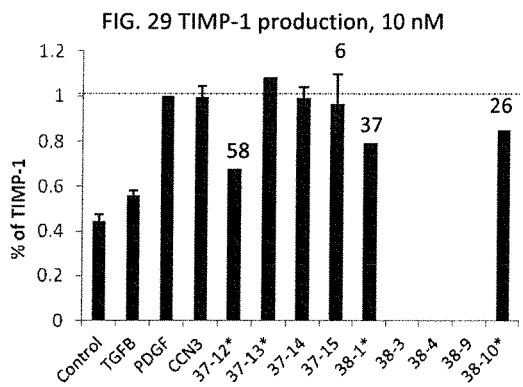

Vertical axis is % of TIMP-1 compared to TIMP-1 in PDGF group. Numbers above bar represent % decrease compared to PDGF group. . * denotes only 1 experiment preformed. Peptides with only 1 experiment have no SE.

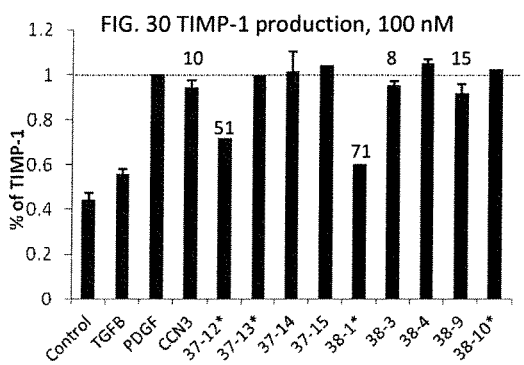

Vertical axis is % of TIMP-1 compared to TIMP-1 in PDGF group. Numbers above bar represent % decrease compared to PDGF group. . * denotes only 1 experiment preformed. Peptides with only 1 experiment have no SE.

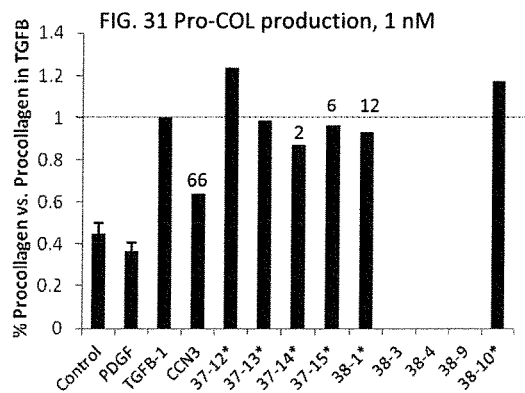

Vertical axis is % pro-collagen type 1 produced compared to that with TGF-beta exposure. Numbers above bars show % decrease compared to TGF-beta group. Error bars are standard error.

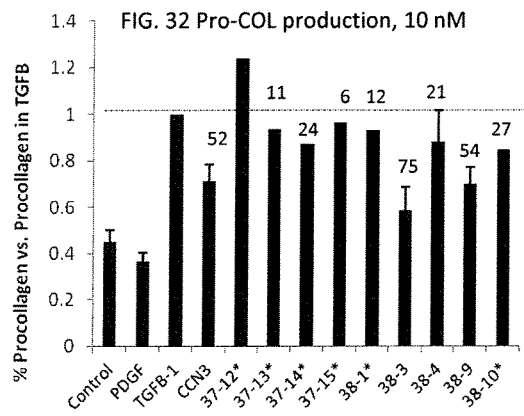

Vertical axis is % pro-collagen type 1 produced compared to that with TGF-beta exposure. Numbers above bars show % decrease compared to TGFB group. Error bars are standard error.

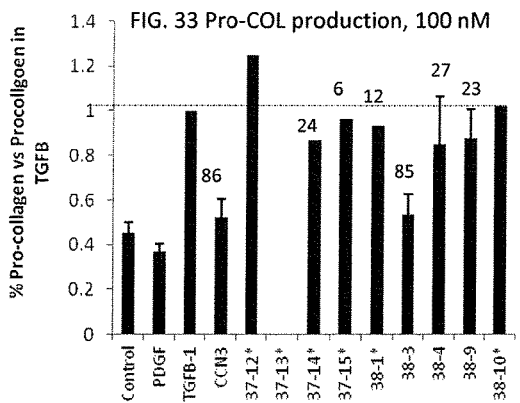

Vertical axis is % pro-collagen type 1 produced compared to that with TGF-beta exposure. Numbers above bars show % decrease compared to TGFB group. Error bars are standard error.

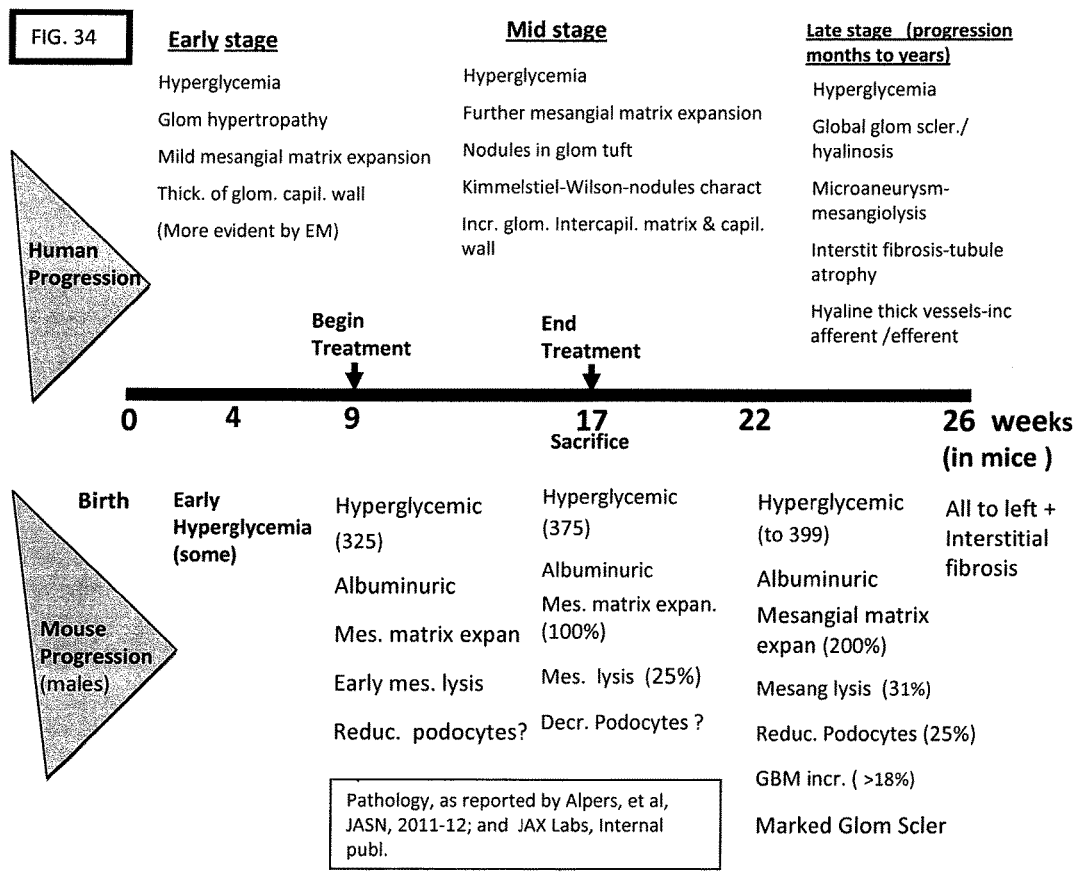

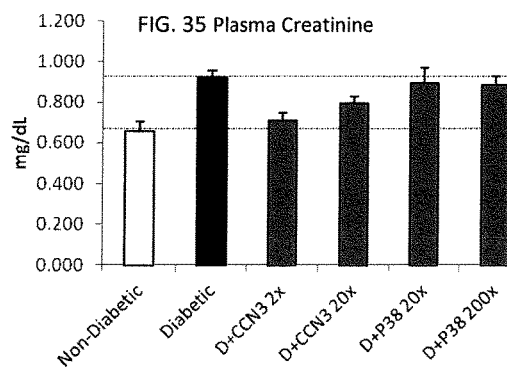
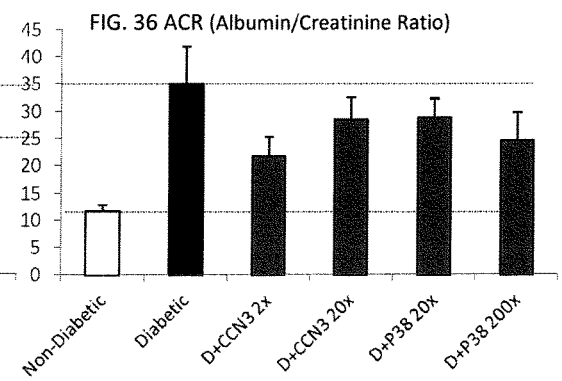
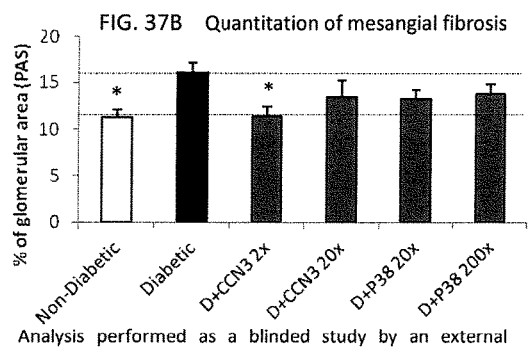
Analysis performed as a blinded study by an external contract lab using non-subjective image analysis system
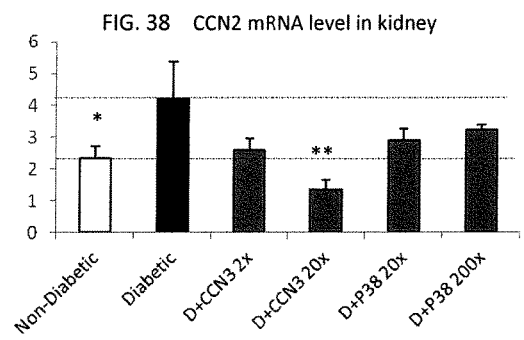
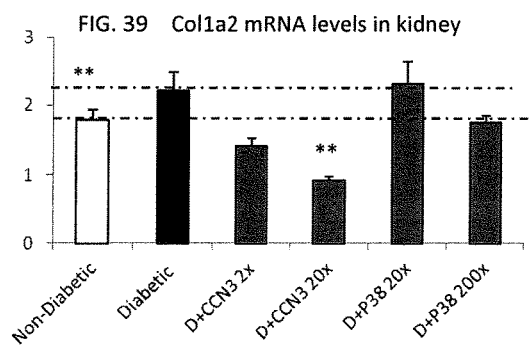
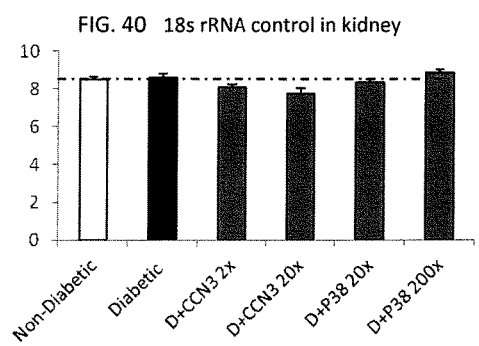

FIG. 37A Qualitative measurement glomerular fibrosis (mesangial expansion)
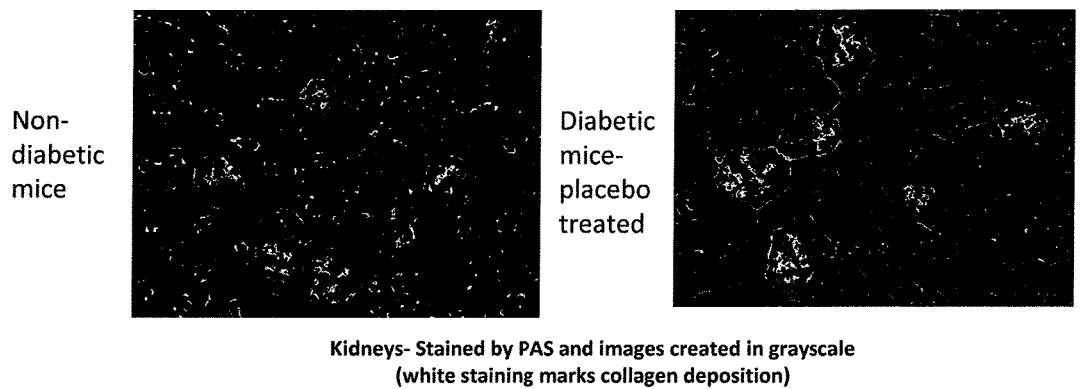
Kidneys- Stained by PAS and images created in grayscale
(white staining marks collagen deposition)

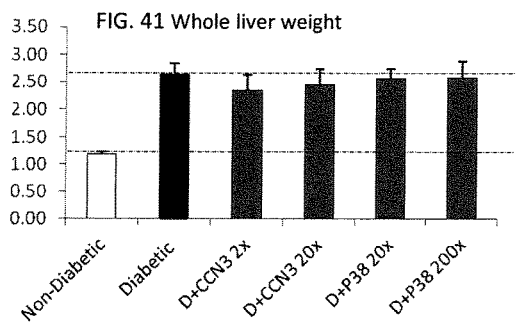
FIG. 41 Whole liver weight
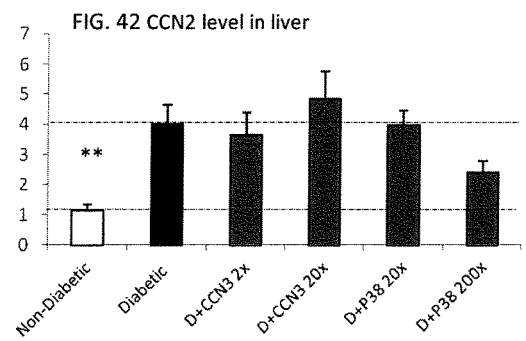
FIG. 42 CCN2 level in liver
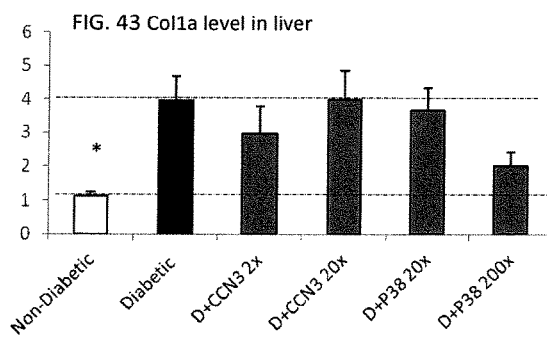
FIG. 43 Col1a level in liver
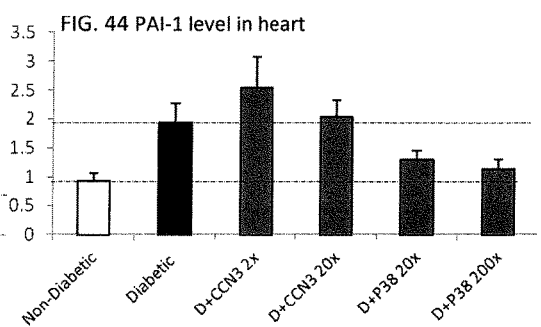
FIG. 44 PAI-1 level in heart

CCN3 AND CCN3 PEPTIDES AND ANALOGS THEREOF FOR THERAPEUTIC USE

CROSS-REFERENCE TO RELATED APPLICATION

This application is a divisional of U.S. patent application Ser. No. 13/725,658, filed Dec. 21, 2012, now U.S. Pat. No. 9,114,112, issued Aug. 25, 2015, which is a continuation-in-part of U.S. patent application Ser. No. 13/079,693, filed Apr. 4, 2011, now U.S. Pat. No. 8,518,395, issued Aug. 27, 2013 which claims priority to U.S. Provisional Patent Application Ser. No. 61/341,694 filed on Apr. 2, 2010, the entirety of each application is incorporated herein by reference and made a part hereof.

FEDERALLY SPONSORED RESEARCH OR DEVELOPMENT

Not Applicable.

SEQUENCE LISTING

The instant application contains a Sequence Listing which has been submitted in ASCII format via EFS-Web and is hereby incorporated by reference in its entirety. Said ASCII copy, created on Aug. 7, 2015, is named 295792-007512_SL.txt and is 33,565 bytes in size.

BACKGROUND OF THE INVENTION

Field of the Invention

The present invention discloses the role of CCN3 in diseases associated with the overexpression of CCN2, which include but are not limited to fibrosis, wound healing and cancer. More particularly, the present invention discloses CCN3 peptides and analogs designed to the function of full-length CCN3 proteins for use in achieving enhanced anti-fibrotic activity thereby blocking fibrosis and or scar development, and for treating cancer and other disease processes where CCN3 and CCN2 are important, and in some cases without unwanted effects of the complete CCN3. The isolated and purified, or synthesized CCN3 peptides and specific analogs are potentially useful in the prevention and/or treatment of diseases by regulating the expression and/or activity of CCN2, CCN3 and other CCN-related proteins, as well as collagen and other extracellular matrix proteins.

The CCN Family of Genes and Proteins

The CCN family of genes presently consists of six distinct members that encode proteins that participate in fundamental biological processes such as cell proliferation, attachment, migration, embryogenesis, differentiation, wound healing, angiogenesis, and several pathologies, including fibrosis and tumorigensis. Proteins encoded by the members of the CCN gene family are primarily 30-40 kDa proteins and are extremely rich in cysteine (10% by mass) (Perbal B., NOV and the CCN family of genes: structural and functional issues. *Molecular Pathology* 54: 57-79, 2001). More recently, it has been reported that some forms of the CCN proteins (CCN3 included) are in the 35-55 kDa range. They are designated as cysteine-rich 61 (CYR-61) proteins, connective tissue growth factor (CTGF) proteins, nephroblastoma overexpressed (NOV) proteins, Wnt-induced secreted proteins-1 (WISP-1), Wnt-induced secreted proteins-2 (WISP-2), and Wnt-induced secreted proteins-3 (WISP-3).

More recently, new nomenclature for this family of genes and proteins has been proposed (see Table 1).

TABLE 1

Proposed Names and Names Currently and Previously Used for CCN Family of Genes and Proteins

| Proposed name | Names used currently or previously |
|---|---|
| CCN1 | CYR61 (human, mouse, *xenopus*), CEF10 (chicken), IGFBP-rP4 (human), βIG-M1 (mouse), CTGF-2, IGFBP10 (human), angiopro |
| CCN2 | CTGF (human, mouse, chicken, *xenopus*), βIG-M2 (mouse), FISP12 (mouse), IGFBP-rP2 (human), Hsc24 (human), IGFBP8 (human), HBGF-0.8, ecogenin (human) |
| CCN3 | NOV (human, rat, chicken, mouse, quail), IGFBP-rP3 (human), IGFBP9 (human), NOVH (human), NOVm, mNOV (mouse), xNOV (*xenopus*) |
| CCN4 | WISP-1 (human), ELM-1 |
| CCN5 | WISP-2 (human), CTGF-L, CTGF-3, HICP, rCOP-1 (rat) |
| CCN6 | WISP-3 (human) |

FIG. 1 shows the modular structure of the CCN proteins, in a very simplistic and linear manner. Although they have a quite conserved multimodular organization, with four modules sharing identity with insulin-like growth factor binding proteins (IGFBPs), Von Willebrand factor (VWC), thrombospondin-1 (TSP1), and a cysteine knot (CT) containing family of growth regulators, the CCN proteins have distinctive biological properties, are differentially regulated, and do not have complete, 100% homology with each other when amino acid sequences are compared. Their involvement has been shown in multiple organ systems. One organ that has been the focus of a large number of studies is the kidney. The underlying mechanisms of action of CCN proteins are still incompletely understood. Attempts to identify unique specific high-affinity signal transducing receptors have been difficult. (Brigstock D. R., Regulation of angiogenesis and endothelial cell function by connective tissue growth factor. *FEBS Letters* 327: 125-130, 2003). However, a number of potential receptors for signaling each perhaps responsible for different activities or functions, have now been tentatively identified (Mason, R., Connective tissue growth factor (CCN2), a pathogenic factor in diabetic nephropathy. What does it do? How does it do it? J. Cell Commun. Signal 3: 95-104, 2009).

CCN2 Gene and its Encoded Protein

Of all the six members of the CCN family, CCN2 has emerged as an important player in its roles in the regulation of certain cellular functions important in skeletal growth, placental angiogenesis and wound healing, as well as its roles in certain diseases including fibrosis (including renal and diabetes associated fibrosis), vascular sclerosis, atherosclerosis, bone disease, vascular resistance, tumorigenesis and/or cancer cell growth.

CCN2 has been now shown to be a causal factor in renal fibrosis, and appears to act in a similar fashion in other fibrotic diseases, including but not limited to, those occurring in the liver, lungs, heart, skin, vasculature and peritoneum (Dean R. G., Balding L., Candido R., Burns W. C., Cao Z., Twigg S. M., Burrell L, M. Connective tissue growth factor and cardiac fibrosis after myocardial infarction. *Journal of Histochemistry & Cytochemistry.* 53(10):1245-56, 2005; Shi-wen X., Pennington D., Holmes A., Leask A., Bradham D., Beauchamp J. R., Fonseca C., du Bois R. M., Martin G. R., Black C. M., Abraham D. J. Autocrine overexpression of CTGF maintains fibrosis: RDA analysis of fibrosis genes in systemic sclerosis. *Experimental Cell Research.* 259(1):213-24, 2000; Ozaki S., Sato Y., Yasoshima M., Harada K., Nakanuma Y. Diffuse expression of heparan sulfate proteoglycan and connective tissue growth factor in fibrous septa with many mast cells relate to unresolving hepatic fibrosis of congenital hepatic fibrosis. *Liver International.* 25(4):817-28, 2005; Sakamoto N., Sugimura K., Kawashima H., Tsuchida K., Takemoto Y., Naganuma T., Tatsumi S., Nakatani T. Influence of glucose and inflammatory cytokines on TGF-beta1 and CTGF mRNA expressions in human peritoneal mesothelial cells. *International Journal of Molecular Medicine.* 15(6):907-11, 2005; Zarrinkalam K. H., Stanley J. M., Gray J., Oliver N., Faull R. J. Connective tissue growth factor and its regulation in the peritoneal cavity of peritoneal dialysis patients. *Kidney International.* 64(1):331-8, 2003.). When expressed in increased amounts, this CCN2 upregulated, for example, by transforming growth factor-β (TGF-β), high glucose concentrations, mechanical stress, advanced glycosylation end products (AGEs), induces (among other things) the overaccumulation of, and sometimes improperly organized, extracellular matrix (ECM) molecules (e.g., collagen forms, and thrombospondin (TSP)). This ECM when organized makes the space separating cells, and includes membranes, connective tissue, and even bone. This abnormal production/accumulation/organization of ECM results in scarring and fibrosis/sclerosis, and improper bone formation including osteoporosis.

Studies with the renal system have provided evidence of the role for CCN2 as an important pathogenic factor in fibrosis/sclerosis in a number of models of chronic kidney disease (CKD). Early reports had suggested a possible interactive role in CCN2 with TGF-β in skin fibrosis and scleroderma (Bradham D M et al, Connective tissue growth factor: a cysteine-rich mitogen secreted by human vascular endothelial cells is related to SCR-induced immediate early gene product CEF-10. *Journal of Cell Biology,* 114:1285-1294, 1991).

The formation of sclerosis or fibrosis in the kidney is a common response to severe or chronic forms of injury. In chronic kidney disease (CKD), there appears to be three predominant causal factors: metabolic, genetic, and hemodynamic. All of these factors can interact, particularly in diabetic nephropathy (DN), to drive progression. CCN2 now appears to be a central, downstream mediator of the effects of these three elements. For example, pathological shear or stretching force resulting from intraglomerular hypertension appears to stimulate the production of cytokines including CCN2. This same force appears to be responsible for increased vascular permeability leading to both proteinuria and an increased production of vasoactive hormones such as angiotensin (AG) II and endothelin, which in turn also elevate CCN2 and further enhance the mechanical force. The abnormal accumulation of advanced glycosylation end products (AGEs) that occur with the altered metabolism of glucose in DN may also work to both directly to increase extracellular matrix (ECM) cross-linking and accumulation, as well as to increase CCN2. The genetic background of the individual can influence the elements of hemodynamics and metabolism and in turn the resulting pathways as described. Additionally, there is a likely influence of genetics on protein kinase C (PKC) activity and production of vasoactive hormones. In all cases, the chronic upregulation of CCN2 activity is likely to result in altered ECM turnover and increasing ECM accumulation, producing fibrosis or sclerosis (In: Contemporary Diabetes: *The Diabetic Kidney,* C E Mogensen & P. Cortes (eds), Humana Academic Publishers, Totowa, N.J., June 2006, Riser, B L et al. CCN2 (CTGF) in the pathogenesis of diabetic renal disease: A target for therapeutic intervention). These findings support the postulate that CCN2 is a central downstream element in the progression of fibrosis, and as such provides a reasonable and novel target for both diagnostics and therapeutic purposes. Additional support for this in renal fibrosis has come from data in humans showing that the level of renal CCN2, and/or that passing into the urine, can be measured and used to predict the onset of renal disease and/or fibrosis as well as to stage progression. This has been supported by a number of reports showing that the level of CCN2 present in the kidney glomerulus, or even passing into urine predicts the future onset, and stages renal disease (including fibrosis) (*Kidney International,* 64:451-458, 2003. Riser, B L et al, CCN2 (CTGF): as a possible predictor of diabetic nephropathy: Preliminary report, *Cytokine,* 47, 1:37-42 2009, F K Tam, et al, Urinary monocyte chemoattractant protein-1 (MCP-1) and connective tissue growth factor (CCN2) as prognostic markers for progression of diabetic nephropathy).

CCN2 is estrogen inducible and overexpressed in steroid-dependent breast or uterine tumors (Tsai et al., Expression and function of CYR61, an angiogenic factor, in breast cancer cell lines and tumor biopsies. *Cancer Research* 60: 5602-5607, 2000; Tsai et al., Expression and regulation of Cyr61 in human breast cancer cell lines. *Oncogene* 21: 964-974, 2000; Sampath et al. Cyr61, a member of the CCN family, is required for MCF-7 cell proliferation: regulation by 17 beta-estradiol and overexpression in human breast cancer. *Endocrinology* 142: 2540-2548, 2001; Sampath et al., Aberrant expression of Cyr 61, a member of the CCN family (i.e. CCN1), and dysregulation by 17 beta-estradiol and basic fibroblast growth factor in human uterine leiomyomas. *Journal of Clinical Endocrinology and Metabolism,* 86: 1707-1715, 2001; Sampath et al, The angiogenic factor Cyr61 is induced by progestin R5020 and is necessary for mammary adenocarcinorma cell growth. Endocrine, 18: 147-150, 2002; Xie et al., Breast cancer, Cyr61 is overexpressed, estrogen-inducible, and associated with more advanced disease. *Journal of Biological Chemistry,* 276: 14187-14194, 2001; Xie et al., Elevated levels of connective tissue growth factor, WISP-1, and CYR61 in primary breast cancers associated with more advanced features. *Cancer Research,* 61: 8917-8923, 2002). CCN2 and other CCN family members are important downstream mediators of estrogen- and progesterone-regulated cell growth. CCN2 and other CCN proteins may also impact other growth regulatory pathways in breast cancer cells. Uterine CCN2 is regulated by both estrogen and progesterone and appears to be important for maintenance or remodeling of stromal ECM (Rageh et al., Steroidal regulation of connective tissue growth factor (CCN2; CTGF) synthesis in the mouse uterus. *Molecular Pathology,* 56: 80-85, 2001; Cheon et al., A genomic approach to identify novel progesterone receptor regulated pathways in the uterus during implantation. *Molecular Endocrinology,* 16: 2853-2871, 2002). In the ovary, CCN2 is regulated by gonadotropins or transforming growth factor-beta (TGF-β) and is associated with thecal cell recruitment and mitosis, and maintenance of the corpus luteum (Wandji et al., Messenger ribonucleic acids for MAC25 and connective tissue growth factor (CTGF) are inversely regulated during folliculogenesis and early luteogenesis. *Kidney International,* 60: 96-105, 2000; Slee et al., Differentiation-dependent expression of connective tissue growth factor and lysyl oxidase messenger ribonucleic acids in rat granulose cells. *Endocrinology,* 142: 1082-1089, 2001;

Harlow & Hillar, Connective tissue growth factor in the ovarian paracrine system. Molecular and Cellular Endocrinology, 187: 23-27, 2002; Harlow et al., FSH and TGF-beta superfamily members regulate granulose cell connective tissue growth factor gene expression in vitro and in vivo. *Endocrinology*, 143: 3316-3325, 2002; Liu et al., Gonodotrophins inhibit the expression of insulin-like growth binding protein-related protein-2 mRNA in cultured human granulose-luteal cells. *Molecular Human Reproduction*, 8: 136-141; 2002).

U.S. Pat. No. 7,780,949 by Riser and DeNichilo discloses the role of CCN2 in the production of extracellular matrix (ECM), as well as methods for diagnosing the presence and progress of pathologies characterized by an accumulation of the ECM components by measuring the level of CCN2 in a sample. The method is directed to diagnosing kidney fibrosis and associated renal disorders, in particular, complications associated with diabetes, hyperglycemia and hypertension.

CCN3 Gene and its Encoded Proteins

CCN3 is another member of the CCN family. It has been reported that CCN3 exists in various forms. In a study to construct retroviral competent ovian recombinants, it has been demonstrated that the CCN3 protein can be expressed either as a full-length protein with a molecular weight of about 50 kDa or a smaller truncated protein, which is a fragment of the full length protein (Perbal B., *J. Clin. Pathol: Mol Pathol.* 54: 57-79, 2001). Other forms of CCN3 protein have also been reported. For example, a CCN3 related protein has been detected at the nuclear envelope of the NCI-H295R cells and another CCN3 related protein binds the promoter of human plasminogen activator inhibitor type 2 (PAI-2) (Perbal B., *J. Clin. Pathol: Mol Pathol*, 54: 57-79, 2001). K19M-AF antibody directed against C-terminal 19-aminoacid peptide of CCN3 revealed at least two conformational states of the native CCN3 protein (Kyurkchiev S. et al., Potential cellular conformations of the CCN3 (NOV) protein. *Cellular Communication and Signaling*, 2: 9-18, 2004). Cytoplasmic and cell membrane bound CCN3 has an exposed C-terminus while secreted CCN3 has a sequestered C-terminus which could be due to interaction with other proteins or itself (dimerization).

The amino acid sequences of the full length CCN3 proteins from various species, including human, have been fully characterized and are disclosed by Li et al. (Li, C. L. et al., A role for CCN3 (NOV) in calcium signaling. *Journal of Clinical Pathology: Molecular Pathology*, 55: 250-261, 2002). One CCN3 full length protein has about 357 amino acids.

U.S. Pat. No. 7,780,949 by Riser discloses that the full-length CCN3 molecule blocks fibrosis in an in vitro model of renal fibrosis by acting, at least partially, through its ability to down-regulate the profibrotic activity of CCN2. CCN3 was not previously known to have activity in fibrosis or wound healing/scarring, either as a positive or negative factor and was not known to have a regulatory effect on CCN2. U.S. Pat. No. 7,780,949 shows that the full-length CCN3 proteins can work to inhibit the production and actions of CCN2, and thus the overproduction of extracellular matrix that characterizes fibrosis in many organs. Neither the above patent, nor other patents or published literature, disclose whether a smaller portion of the whole CCN3, or a peptide, is capable of mediating this activity. It is now understood that fibrosis, although initiated by a variety of different insults, once started appears to follow a common pathway apparently always involving one, or both of TGF-beta and CCN2 as causal factors. Therefore, having shown that CCN3 can be used to prevent and or treat fibrosis and abnormal production/accumulation of ECM e.g., collagen, in renal cells and renal disease, one can reasonably assume that it will be useful in such disease in other organs, and even those initiated by different stimuli or insults. U.S. Pat. No. 7,780,949 further discloses measuring CCN3 levels for diagnosis and prognosis of renal disease.

United States Patent Application Publication No. 2007/0059314 discloses the use of CCN3 or CCN3 fragments having angiogenesis-inhibiting activity for the treatment of pathologies requiring such inhibitory activities. The fragments that exhibit angiogenic-inhibiting activity are approximately 40 to approximately 180 amino acids.

BRIEF DESCRIPTION OF THE DRAWINGS

FIG. 1 shows in a very simplistic manner, the general multimodular structure of the CCN proteins. CT, cysteine knot containing family of growth regulators-like domain; IGFBP, insulin-like growth factor binding protein-like domain; TSP1, thrombospondin-like domain; and VWC, Von Willebrand factor-like domain.

FIG. 2 shows a published mouse sequence of CCN3 (SEQ. ID. No 41) used for design of peptides (upper sequence), and our modified sequence (SEQ. ID. No. 42) with the replacement of cysteines with serines, which does not exist in nature (lower sequence).

FIG. 3 shows specific sequences (peptides 1-40 disclosed as SEQ. ID. Nos. 1-40) that were tested for activity.

FIG. 5 shows the position of the synthesized CCN peptides (CCNp) on mouse CCN3 (SEQ. ID. No. 42) sequence showing the 35 constructed overlapping sequences (CCNp1-35) beginning at the n-terminal end and running to the c-terminal end in black as well as the 5 specifically designed peptides CCNp 36-40 bolded (all here with the cysteines replaced with serines).

FIG. 6 shows the CCN3 sequences chosen for peptide design which were targeted based on their position in the molecule and sequence homology with CCN2. Ultimately, the cysteines were replaced with serine to avoid potential formation of circular structures produced by the charge of the cysteine and thus the obliteration of the normal, or targeted function we were seeking. However, we also did not know if this change would result in complete loss of the functions sought. These peptides were at the same time chosen also for their high homology between human and murine, so that any sequence tested in and proven effective in murine models would be expected to provide a same level of efficacy in humans. FIG. 6 discloses SEQ. ID. Nos. 45-49, respectively, in order of appearance.

FIG. 7A shows the specific CCNp37 (SEQ. ID. No. 37) and CCNp38 (SEQ. ID. No. 38) peptides that were synthesized and tested having the cysteine residues replaced by serine residues.

FIG. 7B is a comparison showing there is 100% homology between murine and human natural sequences of CCNp37 (SEQ. ID. Nos. 48 and 63, respectively, in order of appearance). Also, shown is there is one amino acid difference between native human and mouse CCNp38 sequences, respectively (SEQ. ID. Nos. 50 and 49).

FIG. 7C shows a comparison of naturally occurring human CCN2 and CCN3 sequences at regions selected for CCNp37 and CCNp38. For CCNp37 sequence chosen, both CCN2 and CCN3 have an unusual high homology over these sequences at regions, with only one amino acid difference out of fourteen. In great contrast, for the CCNp38 sequence chosen, CCN2 and CCN3 have an unusually low amino acid homology with only four alike out of fourteen amino acids. FIG. 7C discloses SEQ. ID. Nos. 51 (first item), 63 (second item), 64 (third item) and 50 (fourth item), respectively, in order of appearance.

FIG. 7D shows a comparison of naturally occurring murine CCN2 and CCN3 sequences at regions CCNp37 and CCNp38. For CCNp37 there is no difference from what was shown in 7C above, since there are no differences between human and mouse over this sequence. For CCNp38, there are 4 of 14 amino acids that match the sequence of CCN2 in the naturally occurring sequences. FIG. 7D discloses SEQ. ID. Nos. 48, and 49, second and fourth items respectively, in order of appearance. FIG. 7D discloses SEQ ID NOS 65 and 66, first and third items, respectively, in order of appearance.

FIG. 7E shows peptide sequences with SEQ. ID. Nos. 37, 48 and 63, 54, and 55 in order of appearance.

FIG. 7F shows peptide sequences with SEQ. ID. Nos., from top to bottom of 38, 49, 56, 50, 53, 52, 59, 60, 57, 58, and 61.

FIG. 10A shows CCN2 immunolocalization (reactivity with protein specific antibody) and the inhibitory effect of peptide CCNp37. Here shown, TGF-β treatment results in a dramatic loss (secretion) of the already made CCN2 localized at the cell membrane (dark reddish brown) but also initiates the synthesis of new CCN2, now seen in the cytoplasm (light reddish brown). Along with this, is a phenotype change to a more elongated angular, fibroblast-type cell, characteristic of that seen in fibrosis. Treatment with CCNp37 at 50 nM blocks this phenotypic transition, and reduces greatly the expulsion of CCN2 and synthesis of new CCN2.

FIG. 11B shows collagen I immunolocalization and the inhibitory effect of peptide CCNp38. Treatment with TGF-β (a known pro-fibrotic agent) results in a dramatic loss (secretion) of the abundant collagen I at the cell membrane (shown in the control frame) and the initiation of some new synthesis seen throughout the cytoplasm (TGF-β treated). Along with this is a phenotype change to what appears to be an elongate, less cuboidal, fibroblast-type cell. Treatment with CCNp38 at low concentration of 0.5 nM has little effect. However, at doses of 5-50 nM there is a blockade of the phenotypic transition, the expulsion of some of the premade collagen and new synthesis of collagen that occurs in response to TGF-β. Other peptides did not demonstrate this effect (not shown).

FIG. 12A shows a bar graph of cell proliferation of human chronic myelogenous leukemia in untreated cells (Control) and compared to those pre-incubated with quantities (about 10 nM) of a commercial recombinant CCN3 (rCCN3c) (SEQ. ID. No. 67), full length CCN3 protein made in our laboratory rCCN3 8 (SEQ ID NO: 44), rCCN3 9 (SEQ ID NO: 44), rCCN3 10 (SEQ ID NO: 44), rCCN3 11 (SEQ ID NO: 44), or CCNp37 or CCNp38. CML cells were allowed to grow, then proliferation measured by the CellTiter-Glo®Luminescent Cell Viability Assay Control untreated cells, or cells. The latter is a homogeneous method of determining the number of viable cells in culture based on quantitation of the ATP present, an indicator of metabolically active cells. The commercially produced full length CCN3 produces an approximate 35% reduction in growth and/or viability over the period tested. CCNp37 produces 15-20% inhibition and CCNp38 approximately 40% inhibition, i.e., greater than the effect of full length CCN3.

FIG. 12B shows the tests of CCNp37-1 (SEQ. ID. 37) and CCNp38-1 (SEQ. ID. 38) for their ability to inhibit the growth of chronic myelogenous leukemia cells (CML) in culture and a comparison to rCCN3 (SEQ. ID. NO: 67). Both peptides were able to strongly slow the growth of chronic myelogenous leukemia cell growth.

FIG. 13 demonstrates the increased human skin fibroblast proliferation in response to gadolinium (GAD) a contrast agent used in MRI diagnostics, and thought to cause a pathology termed nephrogenic systemic fibrosis (NSF), when not cleared by the kidneys and deposited in the skin.

FIG. 14 shows that human skin fibroblasts produce and secrete CCN3 in culture under basal conditions, and the exposure to GAD dose-dependently decreases this CCN3 production, while at the same time increasing cell proliferation (compare to FIG. 13). This suggested that CCN3 is able to control fibroblast proliferation. This is important since, NSF, and certain other fibrotic diseases are characterized as fibroproliferative diseases. In these instances proliferation of a key effecter cell results in the overaccumulation of ECM, i.e., collagen, and fibrosis. Previous studies have shown the cytokine platelet derived growth factor (PDGF) production by skin fibroblasts drives the response to GAD. The error bars in the figures represent standard error.

FIG. 15 demonstrates that human fibroblast proliferation is increased by PDGF and this stimulation is blocked by the addition of CCN3 protein as well as CCNp38-3 (Seq. ID. No. 56).

FIG. 16 shows that TGF-beta does not stimulate cell proliferation in this model, and neither CCN3 (SEQ. ID. No. 67) nor CCNp38-3 (Seq. ID. No. 56) has an effect on baseline cell growth, indicating specificity of response. Extracellular matrix (ECM) accumulation is a dynamic process made up of both regulated synthesis and breakdown (ECM turnover). Accumulation or overaccumulation in fibrosis is the result of an imbalance in the two and can therefore be the result of increased synthesis or decreased synthesis rates. However, fibrosis is often characterized by an increase in both synthesis and breakdown, i.e., increased turnover and results from the net difference. Among activities, matrix metalloproteinase 1 (MMP-1) acts to increase breakdown, whereas tissue inhibitors of MMP (e.g., TIMPs) reduce the activity of MMP.

FIG. 17 shows that PDGF exposure also acts to increase MMP-1 activity, whereas CCN3 is able to block that increase. CCNp38-3 (Seq. ID. No. 56) works as well or better than CCN3 protein to accomplish this blockade.

FIG. 18 shows no stimulating effect of TGF-beta and therefore no effect of CCN3 or the peptide.

FIG. 19 shows that PDGF also acts to increase TIMP-1 production and neither CCNp38-3 (Seq. ID. No. 56) nor CCN3 (SEQ. ID. No. 67) is able to block or reduce the increase in TIMP-1 production, showing specificity of response.

FIG. 20 shows that TGF-beta fails to stimulate TIMP-1 production and neither CCNp38-3 or CCN3 have an effect.

FIG. 21 shows that TGF-beta exposure increases pro-collagen production 2-fold or greater and both CCN3 ((SEQ. ID. No. 67) and CCNp38-3 (Seq. ID. No. 56)) completely block the increase.

FIG. 22 shows, human skin fibroblast proliferation in response to PDGF and the effect of 1 nM CCN3 or CCNp peptide as expected, PDGF exposure produced a strong increase in cell proliferation. rCCN3 (SEQ. ID. NO: 67) alone slightly decreased proliferation whereas all of the peptides had a similar or greater reduction (8-22%) in proliferation.

FIG. 23 shows human skin fibroblast proliferation in response to PDGF and the effect of 10 nM CCN3 or CCNp peptide. CCN3 alone produced a 33% reduction in proliferation, whereas the CCNp peptides produced a similar 19-30% inhibition.

FIG. 24 shows human skin fibroblast proliferation in response to PDGF and the effect of 100 nM CCN3 or CCNp peptides. CCN3 alone produced a 46% reduction in proliferation, whereas the CCNp peptides produced a similar 19-36% inhibition. Taken as a whole there was a dose-dependent efficacy of CCN3 and all of the peptides in this group, although there were some differences in the CCNp peptides dependent on the modification.

FIGS. 25-27 show the test results of the effect of modifications in CCNp37 and CCNp38 on their ability to block PDGF stimulated MMP-1 production, as a measure of their effectiveness in blocking skin fibrosis/scarring.

In FIG. 25 CCN3 at 1 nM was able to block little or no MMP-1 production, whereas all of the peptides tested in this series blocked significantly at 1 nM (16-44%). In FIG. 26, the effect of CCN3 at 10 nM was increased (to 27% reduction in MMP-1), whereas the CCNp peptides in some cases increased their activity to as much as 60% inhibition. In FIG. 27 at 100 nM CCN3 reached a 30% reduction in the stimulated MMP-1 production, wheras all CCNp peptides had similar or stronger activity, with CCNp38-3 and CCNp38-4 blocking up to about 60%. All peptide variants were able to block a marked level of MMP-1 production, including those with either cysteine intact or a replacement with serine. When CCNp37 and CCNp38 was made slightly shorter or longer this produced a small change in the effectiveness of the molecule. Some, particularly, CCNp37-15 (SEQ. ID. No. 55) that was slightly reduced in size on the c-terminal end was less effective however.

FIGS. 28-30, show the test results of the same series of peptides for their ability to block PDGF stimulated TIMP-1 production, as a measure of their effectiveness to alter the accumulation of ECM and thus skin fibrosis/scarring. TIMP-1 production is known to be associated with a reduction in ECM breakdown and thus reduced turnover. CCN3 was unable to block the increase in TIMP-1 stimulated by PDGF (FIGS. 29 and 30, CCN3 not tested in FIG. 28). Most of the peptides were also unable to alter the production of TIMP-1. However, CCNp37-12 (Seq. ID. No. 37) and CCNp38-1 (Seq. ID. No. 38) unexpectedly produced approximately 50 and 70% reduction respectively (FIG. 30). CCNp38-3 (Seq. ID. No. 56), 38-4 (Seq. ID. No. 50), and 38-9 (Seq. ID. No. 57) were tested at the high dose only.

FIGS. 31-33 show the test results of the effect of modifications in CCNp37 and CCNp38 on TGF-beta-stimulated human fibroblast pro-collagen production and compared the effect to that of CCN3 (Seq. ID. No. 67), to determine their suitability as therapeutic agents. As expected TGF-beta significantly increased the production of pro-collagen type 1 whereas CCN3 was able to block up from 66 to approximately 86 percent of the stimulated pro-collagen production as the dose was increased (1-100 nM). All of the peptides tested except CCNp 37-12 (Seq. ID. No. 37) were able to reduce the stimulation of pro-collagen type 1 production to some degree. CCNp38-3 (Seq. ID. No. 56) however, was as effective as CCN3 (Seq. ID No. 67].

FIG. 34 shows the method or protocol used to test efficacy of peptide CCNp38 in an animal model of diabetic renal disease. This was carried out using the BT/BR Ob/Ob mouse strain that has a defective leptin receptor that results in increased appetite. As a result mice rapidly gain weight over the control strain and become hyperglycemia at about one month of age going on to develop renal disease resembling that in humans. This is regarded by some to be the best rodent model for mirroring renal disease in humans as a complication of diabetes. Animals were treated with either rCCN3 (SEQ. ID. NO: 67) or CCNp38 (SEQ. ID. 38) beginning at 9 weeks of age, when early renal disease has been documented. Mice were treated for 8 weeks, then sacrificed and measured for renal disease and other complications, and the effect drug treatment. Shown below the time line in the figure are the reported renal disease characteristics, and thus the expected manifestations of disease. Shown above the time line is the comparable progression in humans.

FIG. 35 shows that 17 weeks of diabetes elevates plasma creatinine, substantiating impaired renal function, and 8 weeks of treatment with CCN3 (SEQ. ID. NO: 67) or CCNp38 (SEQ. ID. 38), reduces or blocks this impairment.

FIG. 36 shows that 17 weeks of diabetes elevates the albumin to creatinine ratio, substantiating protein leakage and renal damage, and 8 weeks of treatment with CCN3 or CCNp38 greatly blocks this renal damage as evidenced by the lack of change.

FIG. 37A shows qualitatively by PAS staining, in gray scale that 17 weeks of diabetes results in mesangial expansion, substantiating renal fibrosis (white stain shows collagen deposition). FIG. 37B shows quantitatively by image analysis of multiple PAS stains (3 sections per mouse/7-9 mice per treatment group) that 17 weeks of diabetes results in mesangial expansion, substantiating renal fibrosis., and 8 weeks of treatment with CCN3 or CCNp38 greatly blocks this pathology.

FIG. 38 shows that renal mRNA levels for the fibrosis gene CCN2 are increased by diabetes, and treatment with CCN3 or CCNp38 greatly reduces or blocks the increase, thus treating the disease.

FIG. 39 shows that renal mRNA levels for the fibrosis gene Col1A2 are increased by diabetes, and treatment with CCN3 or CCNp38 greatly reduces or blocks the increase, thus treating the disease.

FIG. 40 shows that renal mRNA levels for the control 18S rRNA are not increased by diabetes as expected, and treatment with CCN3 or CCNp38 has no effect on levels as expected.

FIG. 41 shows that liver weight is greatly increased by 18 weeks of diabetes, and treatment with CCN3 or CCNp38 slightly reduces this increase.

FIG. 42 shows that liver mRNA levels for the fibrosis gene CCN2 are increased by diabetes, substantiating an inflammatory response and initiation of fibrosis, treatment with CCN3, but particularly CCNp38 greatly reduces or blocks the increase in a dose-dependent manner.

FIG. 43 shows that liver mRNA levels for the fibrosis gene Col1A2 are increased by diabetes, substantiating the initiation of fibrosis, treatment with CCN3 reduced, but again CCNp38 dose-dependently blocked the increase in collagen.

FIG. 44 shows that heart mRNA levels for the fibrosis gene plasminogen activator inhibitor 1 (PAI-1) are increased by diabetes, substantiating the initiation of fibrosis, treatment with CCNp38 greatly reduces, and at the high dose blocks the increase,

DETAILED DESCRIPTION OF THE INVENTION

Figure 4:
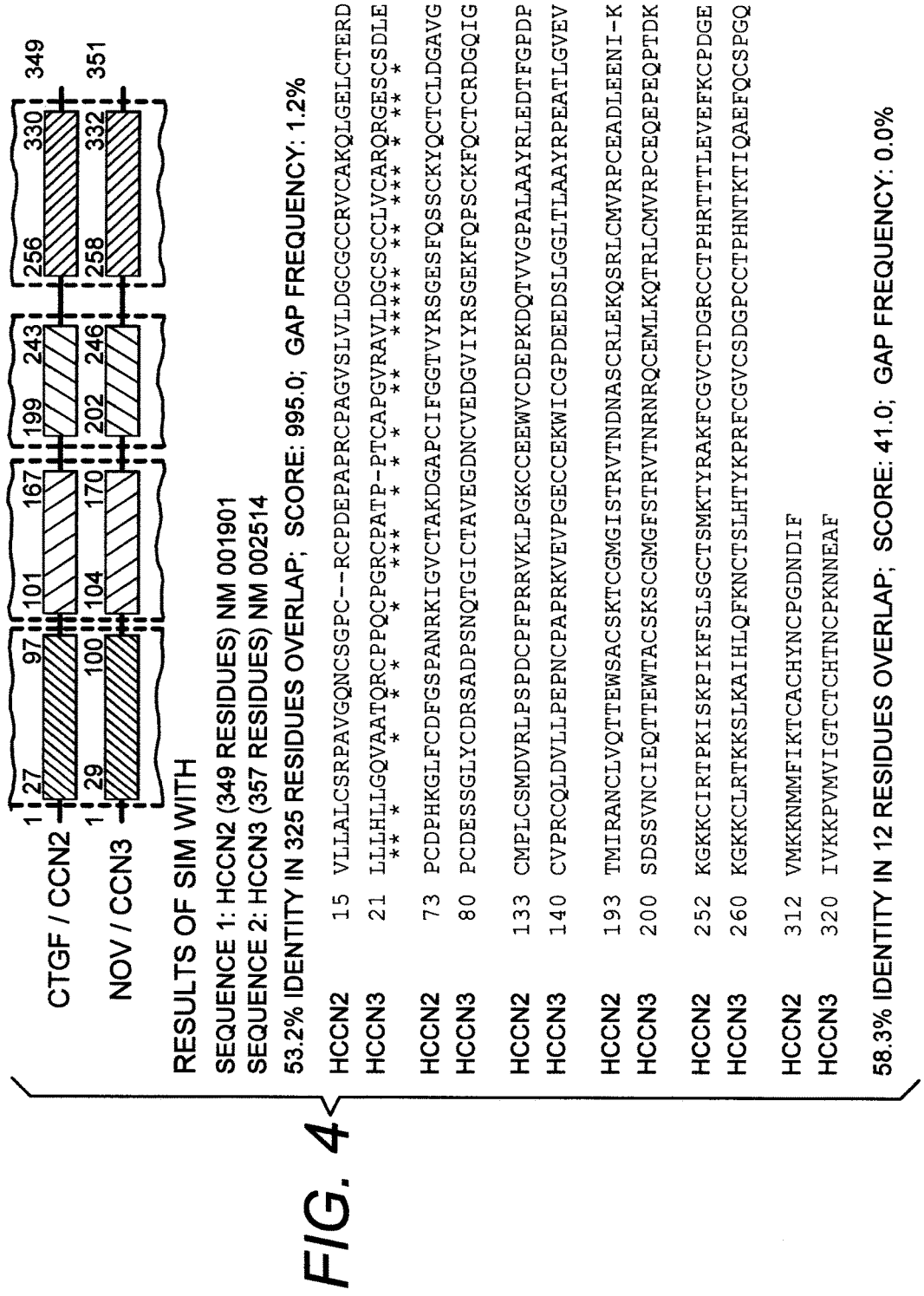
FIG. 4 shows the overall structure and sequence alignment of human CCN (hCCN), showing both hCCN2 (SEQ. ID. No. 43) and hCCN3 (SEQ. ID. No. 44) as the computer aligned them, with a schematic diagram of the four described modules shown in the upper part of the figure, including IGF-BD, VWF, TSP and the c-terminal repeat element. The lower portion of the figure shows the sequence alignment (marked by asterisks) of the two molecules (hCCN2 and hCCN3) here with the cysteines intact.

While this invention is susceptible of embodiments in many different forms, there is shown in the figures, and will be described herein in detail, specific embodiments thereof with the understanding that the present disclosure is to be considered as an exemplification of the principles of the invention and is not intended to limit the invention to the specific embodiments illustrated.

The present invention is directed to isolating newly described, newly produced, specific, effective CCN derived peptides, as a substitute for the full-length CCN3 protein, to achieve equal or better anti-CCN2 and anti-fibrotic activity, also producing novel manufacturing and delivery advantages. In a preferred form of the invention, it was surprisingly found that a small number of peptides having from about 12 to about 20, more preferably 12 to about 18 and most preferably 12 to about 15 amino acids and most preferably fourteen amino acids in human, mouse and rat native sequences and in analogs of the same where native cysteine residues are substituted with a replacement amino acid are able to mimic specific activities of CCN3. In a preferred form of the invention, the replacement amino acids are selected from serine, alanine, glycine, S-methylated cysteine or a combination thereof. Most preferably, the replacement amino acid is serine. These peptides were effective in treating pathologies associated with the over-accumulation, disregulation of turnover, or altered composition, of extra-cellular matrix proteins. These short peptides are far smaller than the full-length CCN3 protein, the naturally occurring one-half and one-quarter length CCN3 fragments reported in the literature, and the artificially prepared 40 to 180 amino acid fragments disclosed in the '314 published patent application discussed above, and are likely to be more easily synthesized and formulated for delivery to a patient in need thereof. Sometimes these small peptides may be referred to as "CN" followed by a number, e.g., CN38 as a shorthand for CCNp38.

Selection of the CCN3 Peptides

The present invention discloses a role of CCN3, or CCN2, derived peptides in among others, diseases associated with the over-accumulation, disregulation of turnover, or altered composition of extracellular matrix molecules in a human subject, which can lead to fibrosis, scarring, abnormal wound healing and cancer cell/tumor growth and metastasis. Certain CCNp peptides of the present invention can be used, in some cases, as a substitute for full-length CCN3 protein, to achieve equal or greater anti-fibrotic activity. The term "fibrosis" used in the present disclosure is used interchangeably with the term "sclerosis" and "scar formation" since they are similar processes involved in the overgrowth of fibrous or fibrosis-like tissue and/or the increased, abnormal deposition and/or assembly/organization of extracellular matrix molecules such as collagen, and all may have CCN2 as at least a causal factor.

In order to isolate the CCN peptides, a series of 36 short overlapping peptide sequences, beginning at, and defined by, the n-terminal region and working to the c-terminal end of the CCN3 were generated. Short overlapping sequences are defined herein as sequences ranging in size from about 12 to 20 amino acids and more preferably 12 to 18 amino acids even more preferably 12-15 amino acids and most preferably 14 amino acids (or any range or combination of ranges therein) and overlap each other on the full-length protein sequence by about 3 to 7 amino acids. Murine (rodent) models of fibrosis were first used to verify fibrotic activity; therefore murine CCN3 sequences were used. It is well-known in the art that human CCN3 has a strong homology with rodent. In fact, the mouse and the human sequences for the region chosen for peptide CCNp37 are identical, whereas for CCNp38 there is only a single amino acid difference between the human and the mouse. FIG. 2 shows the published mouse CCN3 sequence and the location of cysteine residues that were replaced here by serine residues, in order potentially to aid in the prevention of circularization of the peptides, and loss of activity. On the negative side, this substitution could also have the potential to eliminate all biological activity ascribed to CCN3, especially since it is known to be a "cysteine-rich molecule" and its known function would therefore be expected to be dependent on the presence of cysteines. The effect(s) of this change could not be predicted before our work. The cysteine-modified peptide sequences shall sometimes be referred to as analogs or serine analogs of CCN3 native sequences. FIG. 3 shows the sequence of the overlapping peptides that were synthesized and tested (peptides designated CCNp1-35).

The following table coordinates the peptide numbers with the SEQ. ID. Nos. and a representative figure where the sequence is shown.

| SEQ. ID. NO. | DESCRIPTION | REPRESENTATIVE FIGURE |
|---|---|---|
| 1-40 | CCNp1 through CCNp40 | See FIG. 3 |
| 41 | Mouse native CCN3 full-length | See FIG. 2 |
| 42 | Mouse analog CCN3 full-length with native cysteines replaced with serines | See FIG. 5 |
| 44 | Human native full-length CCN3 | See FIG. 4 |
| 45 | Mouse native CCNp39 206-220 | See FIG. 6 first item |
| 46 | Mouse native of CCNp40 213-227 | See FIG. 6 second item |
| 47 | Mouse native CCNp36 | See FIG. 6 third item |
| 63 and 48, respectively | Human and mouse native CCNp37 289-302 | See FIG. 6 fourth item and FIG. 7C second item |
| 49 | Mouse native CCNp38 84-98 | See FIG. 6 last item |
| 50 | Human native CCNp38 | See FIGS. 7B and 7C |
| 51 | CCN2 native fragment with high homology with native CCN3 | See FIG. 7C |
| 52 | Rat native CCNp38 | See FIG. 7F |
| 53 | Rat analog CCNp38 with native cysteines replaced with serines | See FIG. 7F |
| 54 | Human or mouse analog CCNp37-14 with native cysteines replaced with serines and without FS on N-terminal end | See FIG. 7E |
| 55 | Human or mouse analog CCNp37-15 with native cysteines replaced with serines and without PH on C-terminal end | See FIG. 7E |
| 56 | Human analog CCNp38-3 with native cysteines replaced with serines | See FIG. 7F |
| 57 | Human analog CCNp38-9 with native cysteines replaced with serines and minus CD (or SD) at N-terminal end | See FIG. 7F |
| 58 | Human analog CCNp38-10 with native cysteines replaced with serines and with added T on C-terminal end | See FIG. 7F |
| 59 | Mouse analog CCNp38-7 with native cysteines replaced with serines and without CD or (SD) at N-terminal end | See FIG. 7F |
| 60 | Rat analog CCNp38-8 with native cysteines replaced with serines and without CD or (SD) at N-terminal end | See FIG. 7F |
| 61 | Human native CCNp38-11 with a T added to the C-terminal end | See FIG. 7F |
| 62 | Human analog full-length CCN3 with native cysteines replaced with serines | None |

Since CCN2 and CCN3 are members of the same family, but possess different apparent biological functions (in the case of effect on collagen it was found opposite activities), this suggested to us that at least one mechanism for the observed blocking activity of CCN2 (and downstream collagen production) might be due to receptor competition. That is, CCN3, or a part of it, might interact with a CCN2 receptor preventing or interfering with CCN2-mediated signaling. That is, CCN3 might possess a sequence that is recognized by the CCN2 receptor, but when bound to it, would not allow signaling for increase matrix production or accumulation, i.e., it could act as a natural, competitor. This was not an obvious mechanism, however, because we also found that CCN3 also greatly inhibited CCN2 synthesis, so it remained possible that the activity was not due to a receptor blockade, but instead due to an inhibition in the production of CCN2. Nevertheless, the two proteins, CCN3 and CCN2, were examined for similarities and differences in amino acid sequence (structure), after producing a computer-generated "best-fit" alignment as shown in FIG. 4 starting with the human sequence. For the reasons hypothesized above, four regions with very high complementary in amino acid sequences (i.e., between CCN2 and CCN3) were found and chosen from both the TSP-like element (referred to as CCNp39, CCNp40, and CCNp36) and the C-terminal module (referred to as CCNp37) (FIGS. 4 and 5). Also selected was one region within the insulin-like growth-factor binding domain of CCN3, referred to as CCNp38, where it was observed that CCN3 and CCN2 had unusually low (14% in murine, 28% in human) complementary over a relatively large region (shown in FIGS. 4 and 5). It was possible that this unique difference discovered might be responsible for the different actions of CCN2 versus CCN3, and might work to block CCN2, work independently, or in addition to CCN2 blockade. All of the peptide sequences, namely CCNp39, CCNp40, CCNp36, CCNp 37 and CCNp38, were further reduced by replacing any cysteine residues with serine residues. Consequently, such serine modified peptide sequences are derived from CCN3 sequences and could possibility possess similar anti-fibrotic activity as we observed with the full-length protein. It is also contemplated that the cysteine residues could also be replaced by alanine, glycine, S-methylated cysteine or combinations thereof (including serine) to produce similar activity.

The present invention contemplates that the CCN3 peptide sequences and their analogs discovered have the same, similar, or greater CCN2 inhibitory, and ECM (e.g., collagen) regulating activity as the full length protein. As discussed in further detail below, we were surprised to find that two short peptides, CCNp37 and CCNp38, demonstrated significant CCN2 inhibitory activity while the 38 other peptides screened were not effective in inhibiting CCN2 expression. Thus, these peptides are unique and useful in the treatment of pathologies associated with the over-accumulation, disregulation of turnover, or altered composition of extracellular matrix molecules in the subject.

FIG. 6 shows the sequences chosen for the 4 specifically designed and made peptides (36-40) and states the approximate homology to the best matching of the CCN2 sequence. Three were chosen for their high homology (CCNp37, 39, 40) to CCN2 sequences, one for its low homology (CCNp38), and one for its average (50%) homology (p36). More particularly, FIG. 7A shows peptide sequences CCNp37 and CCNp38 that were selected and synthesized by replacing the cysteine residues with serine to possibly prevent circularization of the molecule and loss of activity. As discussed above, murine peptides were selected for testing because of its high degree of homology with humans which is illustrated in FIG. 7B, and the use of murine models to demonstrate efficacy, predicting the human response. The human equivalent sequence to the tested murine CCNp38 is shown in FIG. 7B bottom. There is only one amino acid difference between this sequence in humans and mice (bottom sequence FIG. 7B and bottom sequence FIG. 7D). Finally, FIG. 7C and FIG. 7D demonstrate that while a strong homology exists between CCN2 and CCN3 at the peptide sequence of CCNp37, that same homology does not exist at peptide sequence CCNp38.

Results from the Screening of Selected CCN3 Peptides

The peptides selected above, and shown in FIG. 5, were synthesized and tested in the three different in vitro assays constructed to model fibrosis, or fibrosis-related pathology in vivo for anti-fibrotic activity. These assays have been used extensively by us and by others, and are highly predictive of related responses in vivo, including those occurring in humans. One in vitro assay, i.e., of cell adhesion in vitro was used. There is a requirement for adhesion in wound healing and fibrosis, with cells responding to the binding of CCN2 to their receptors for other critical activities. Also alteration of cell attachment and receptor binding is implicated in other non-fibrotic diseases, previously named in this application. For this adhesion assay, a well of a culture plate was coated with CCN2 protein and then rat mesangial cells were added for a defined period. Since the mesangial cells possess CCN2 receptors, they bind tightly to the plate via the specific receptor and therefore adhesion via this receptor can be measured. After a standard period of incubation, the cells are washed to remove non-attached cells. These adherent cells are then removed and counted to determine the percent of the total cells that adhered. The ability of each peptide to block this binding was examined by preincubating cells with the peptide of interest. Controls were used for comparison without CCN2 coating.

In a second assay, the ability of the peptide to block the stimulation of collagen type I promoter by TGF-beta was tested. Collagen type I upregulation is a characteristic feature of fibrosis and is often used as an end point determination. TGF-beta is a well-established pro-fibrotic factor or cytokine that mesangial cells and other cells in the fibrotic response respond to by upregulating collagen and other matrix molecule production and accumulation. Several new anti-fibrotic therapies are under development that target the activity of TGF-beta. For the assays used in connection with the present invention, collagen promoter activity was measured as a rapid and early indicator of collagen-related fibrotic activity. The cells in culture were either unstimulated or stimulated by TGF-beta, both in the presence and absence of the selected peptides. If the peptides have inhibitory activity, the promoter activity under TGF-beta stimulation would be reduced to some value approaching the control, non-TGF-beta treated cells. The collagen promoter assay is based on the transfection of mesangial cells with a COL 1a2 promoter linked to luciferase. Therefore, when the promoter is stimulated it can be measured as luciferase units (Riser et al, *CCN3 is a negative regulator of CCN2 and a novel endogenous inhibitor of the fibrotic pathway in an in vitro model of renal disease*, American J Pathology, 174, 5, 2009). The level of collagen promoter activation (in arbitrary units), is based on a transfection efficiency control (CMV promoter activation).

In a third assay, and immunochemical staining was developed that allowed for measuring cellular changes in response to TGF-beta stimulation in both the amount and distribution of CCN2 as well as collagen type I (a protoypical ECM molecule altered in fibrosis, atherosclerosis, vascular calcification, bone disease, and other related disease). This assay also allows one to determine if there is a phenotype change of the cells, particularly to a more fibroblastic-like cell. This change is characteristic in fibrosis; not only in mesangial cell in renal fibrosis but also other cell types can cause fibrosis. This assay is therefore applicable to test the effect of synthesized peptides (Riser et al, *CCN3 is a negative regulator of CCN2 and a novel endogenous inhibitor of the fibrotic pathway in an in vitro model of renal disease*, American J Pathology, 174, 5, and 2009).

Figure 8:
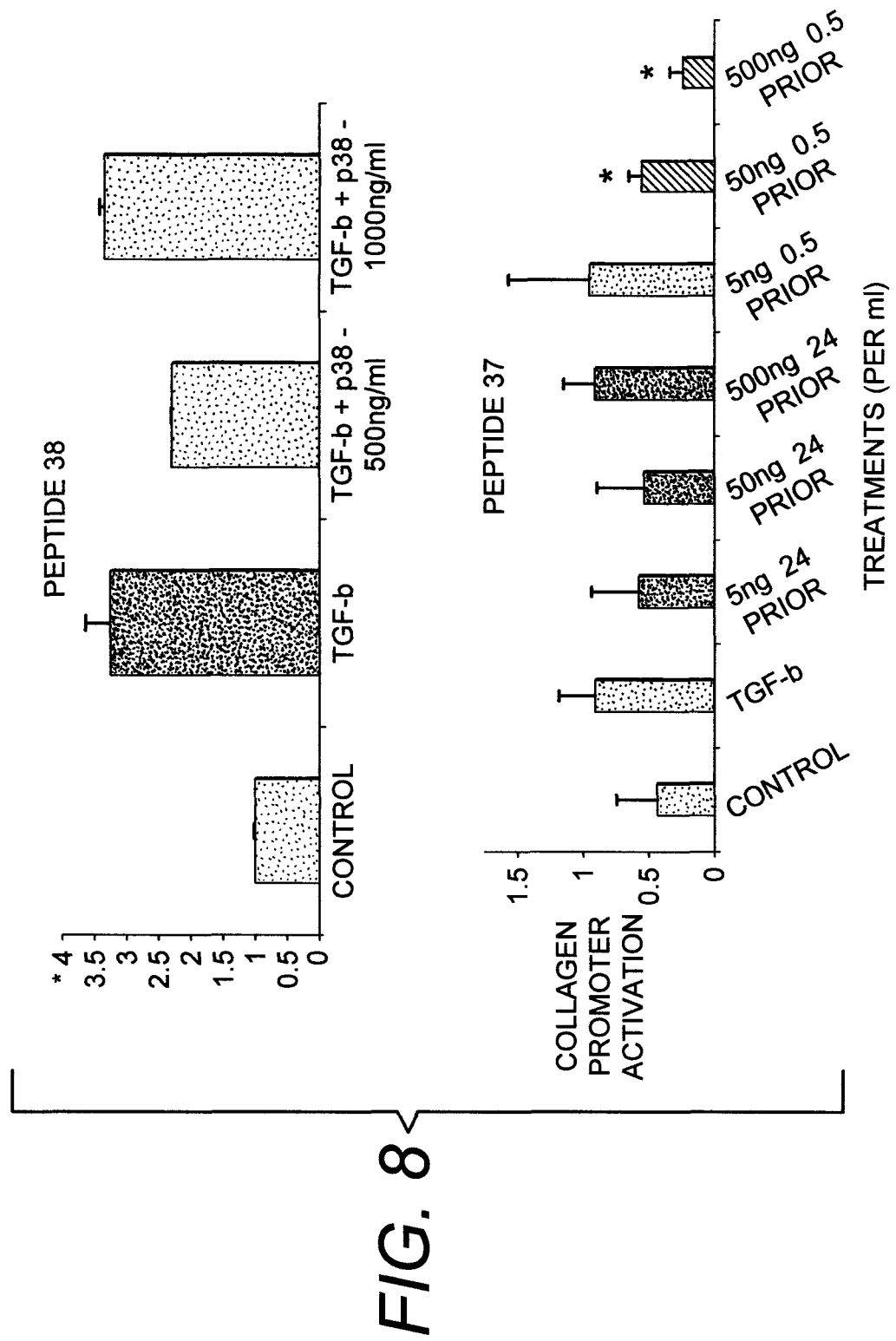
FIG. 8 shows that CCNp37 and CCNp38 reduce collagen promoter stimulation by TGF-β. Peptide 38 (TOP) was able to inhibit collagen promoter activity at 500 ng/mL. Peptide 37 demonstrated an ability to totally block TGF-β-stimulated collagen promoter activity when added just prior to TGF-β (right 3 bars in lower figure). This inhibitory activity was also present (although to a lower level) even when added 24-hours prior to TGF-β. None of the other 38 peptides made and tested showed activity in this assay, so the data are not shown. The Y-axis in the top figure is the level of collagen promoter activation (in arbitrary units), based on a transfection efficiency control (CMV promoter activation), as also shown in the lower figure.
Figure 9:
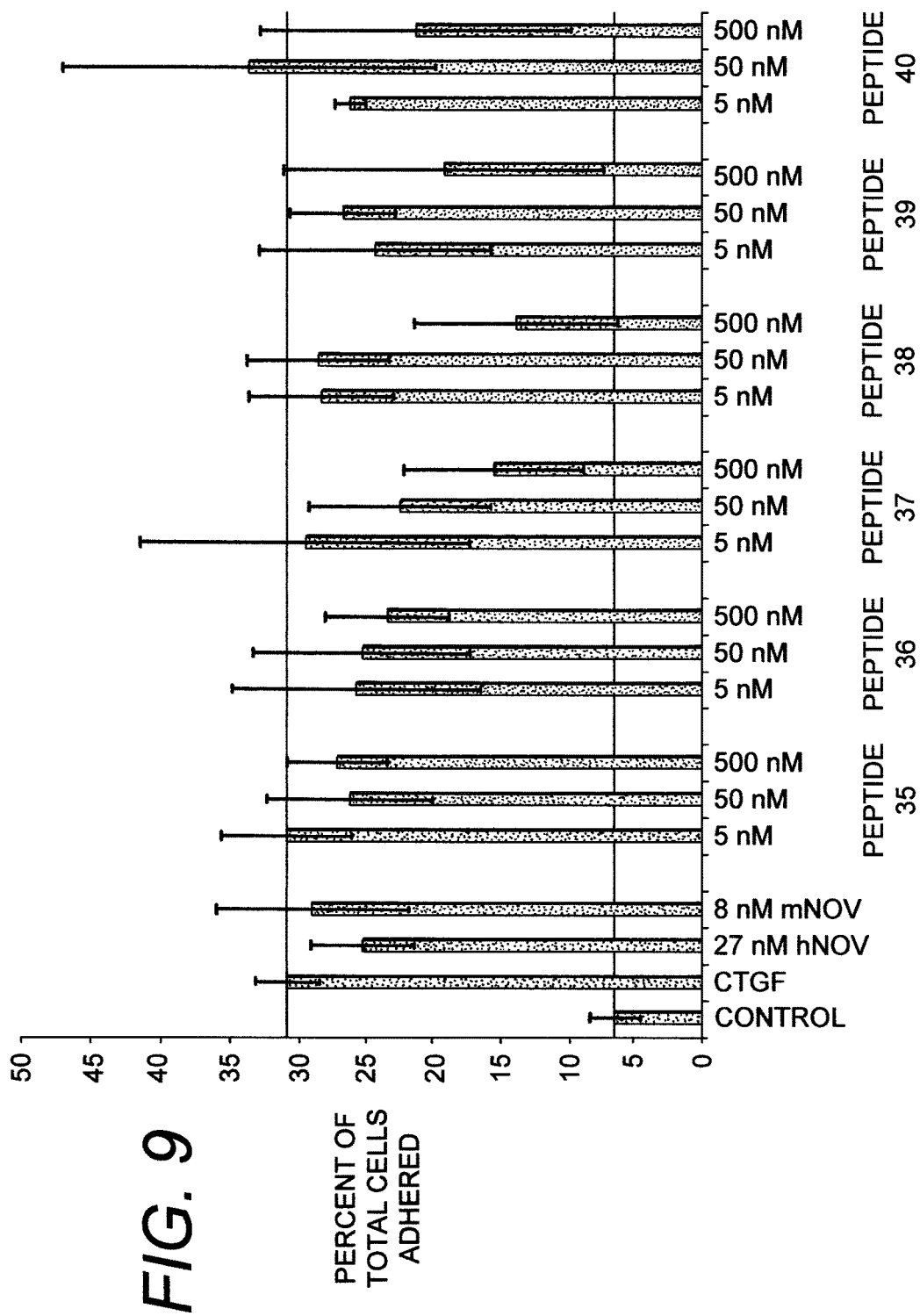
FIG. 9 shows CCNp37 and CCNp38 dose-dependently blocking the cellular adhesion to CCN2 coated plates. Control plates show the adhesion of rodent mesangial cells to plastic only (uncoated) plates. "CTGF" or CCN2, the second bar from the left, shows the marked increased adhesion mediated by cellular receptor binding to CCN2-coated plates, as opposed to that occurring on the uncoated plastic. Full-length CCN3 (NOV) human (27 nM) added just prior to the treatment with TGF-β, provided some inhibition of this binding as expected. However, peptides CCNp37 and CCNp38 dose-dependently blocked the receptor binding mediated to CCN2, providing approximately 60% to 70% inhibition at the highest concentration tested (500 nM). This indicates that the two peptides are each able to interact at the binding site. None of the other 38 peptides tested (only p35, p36, p37 and p40 of those shown here for space considerations) were able to as strongly block binding. The specific activity shown for peptides CCNp37 and CCNp38 in this assay demonstrate an ability to block the receptors on the cells that would bind CCN2, and would be required for specific activities. Cellular adhesion and the binding of the peptide to the receptor for CCN2 is critical to normal physiology and numerous pathological states.
Figure 10B:
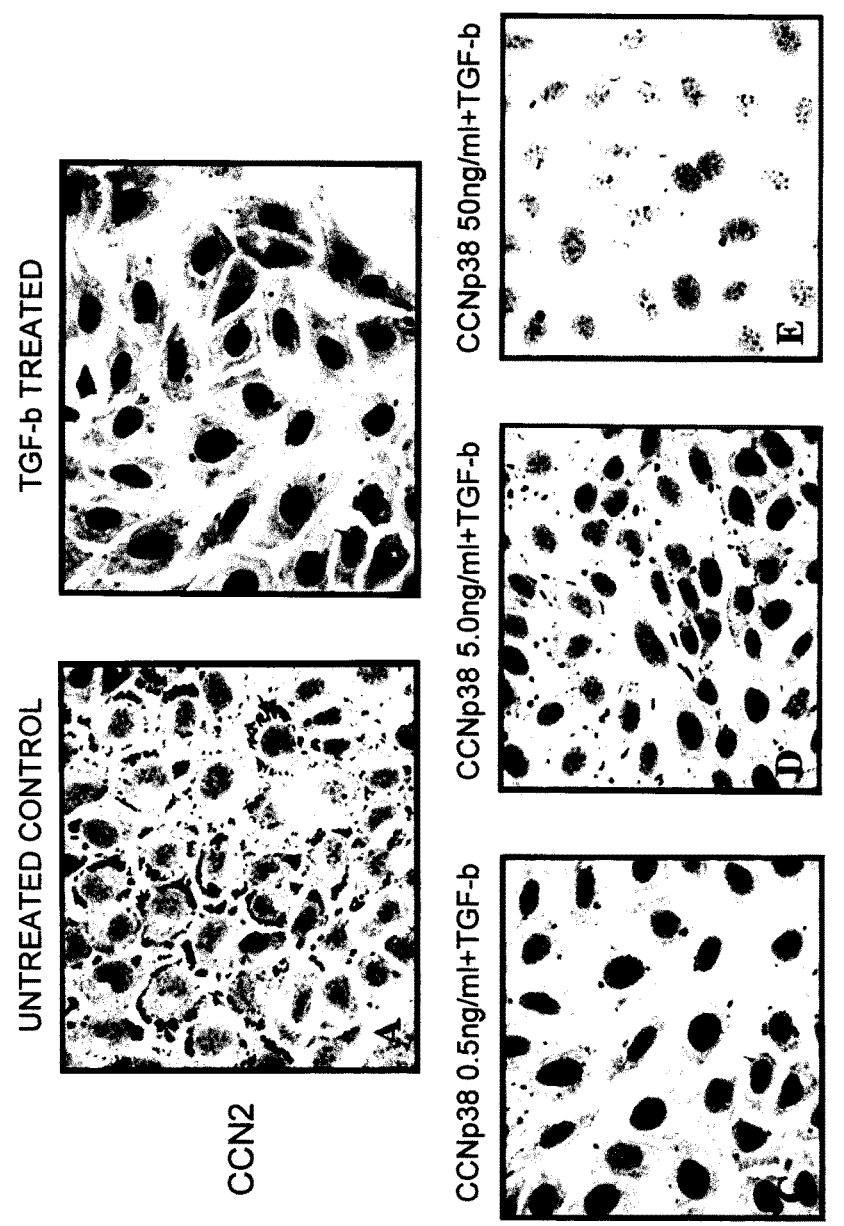
FIG. 10B shows CCN2 immunolocalization and the inhibitory effect of peptide CCNp38. The untreated control cells show extensive CCN2 (brown) at the cell borders. TGF-β treatment results in a dramatic loss (secretion) of CCN2 at the cell membrane and the initiation of new synthesis now seen throughout the cytoplasm. Along with this is a phenotype change to what appears to be a fibroblast-type cells, characteristic of fibrosis. Treatment with CCNp38 blocks this phenotypic transition, the expulsion of CCN2, and new synthesis of CCN2. The optimal effect appears to be at 50 nM, with a dose response effect occurring with lower concentration. Other peptides did not produce this effect (not-shown).
Figure 11A:
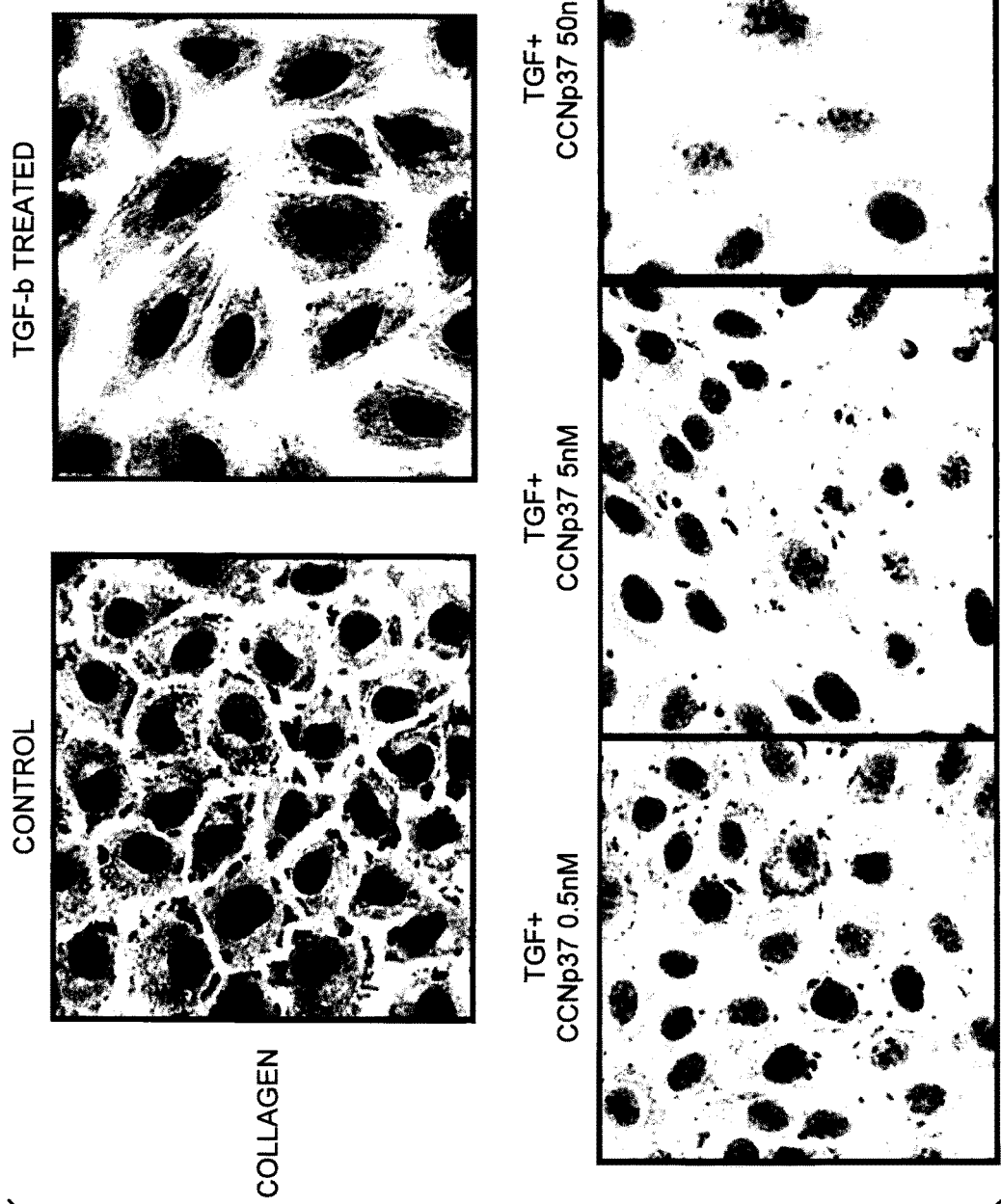
FIG. 11A shows collagen I immunolocalization and the inhibitory effect of peptide CCNp37. TGF-β (a potent stimulator of collagen accumulation and fibrosis) treatment results in a dramatic loss or secretion of the abundant collagen I at the cell membrane (shown in the control frame as brown or reddish brown) and the initiation of some new synthesis seen throughout the cytoplasm (TGF-β treated). Along with this is a phenotype change to what appears to be an elongate, less cuboidal, fibroblast-type cell characteristic of fibrosis. Treatment with CCNp37 at a low concentration of 0.5 nM blocks this phenotypic transition, the expulsion of CCN2 and new synthesis of CCN2. Higher doses show the same or similar effect. Other CCNp peptides tested did not show this effect (not shown).

The results from the peptide screens showed no significant inhibition of CCN2-mediated binding or of collagen promoter-inhibitory activity for any of the 36 overlapping peptides in either the collagen promoter or the CCN2-mediated adhesion assay. For peptide 37 (CCNp37) designed to a specific region in the c-terminal module with high (nearly 100%) complementary, both inhibition of TGF-beta stimulated collagen promoter activity (FIG. 8) was found, as well as inhibition of receptor binding (adhesion to CCN2) (FIG. 9). CCNp37 appeared to be more potent than CCNp38 in inhibiting collagen promoter activity, and treatment immediately prior to TGF-beta was most effective (bottom figure right), however, even a 24 hour prior exposure was able to produce some activity (bottom center). CCNp37 and p38 also had marked, and similar effectiveness in inhibiting TGF-beta stimulated adhesion to CCN2. This demonstrates a dose-dependent ability of CCNp37 and CCNp38 to interfere with CCN2 binding to its cellular receptor. None of the overlapping peptides or those other specifically designed peptides showed any consistent inhibitory activity. Some peptides were even observed to enhance the promoter activity. CCNp38 has remarkably low complementary to CCN2 and is found in the IGFBD domain. This positive effect of CCNp37 and CCNp38 was also found when examined during immunohistochemical staining assay. CCNp37 (FIG. 10A) and CCNp38 (FIG. 10B) were able to block the redistribution and new synthesis of CCN2 in a dose-dependent manner indicating an effect on both production and activity of CCN2, and appeared to also block the transition to a fibroblast-type cell, and important factor in the transition of cells to a phenotype important in the generation and progression of fibrosis in many organ systems. A similar blockade effect on collagen type I was observed and occurred with both CCNp37 (FIG. 11A) and CCNp38 (FIG. 11B). The present invention therefore demonstrates for the first time, a method to block CCN2 synthesis and activity, cell binding or adhesion to CCN2, collagen accumulation, mesangial cell transition to a fibroblast-type cell and thus fibrosis, using unique small peptides from very limited selective regions of the full-length CCN3 protein. Consequently, the CCN3 peptide of the present invention may be also be used to block CCN2 mediated stimulation of cancer cell growth and to promote wound healing with minimal scarring. Since CCN2 is well-known as a key factor in the progression of a number of diseases, the ability to block this factor by such peptides has far reaching therapeutic applications. It was unexpected finding that one region with near total complementary and one different region with little or no complementary were both effective at blocking adhesion, CCN2 activity, adhesion and collagen activity. These findings and activities could not be predicted.

One of the potential uses of the method in the present invention is for the treatment of fibrosis. The term "fibrosis" used in the present disclosure includes fibrosis and/or sclerosis and scarring since they are similar processes and virtually all have been shown to have CCN2 as at least one causal factor. In the present disclosure, "fibrosis", "sclerosis" and "scarring" can be used interchangeably. The fibrosis can be associated with any organ capable of forming fibrosis, such as (but are not limited to) kidney, heart, liver, lungs, vasculature (including scleroderma, coronary arteries), skin, cervix, edometrium, eye, gums, brain, and the peritoneum. The fibrosis can also be the result of one of the pathological conditions such as (but are not limited to) renal diseases, peritoneal dialysis, macular degeneration, periodontal disease, congestive heart failure, cardiac ischemia and cardiac hypertrophy, stroke and related ischemia and reperfusion injury, surgical and medical intervention procedures (e.g., balloon angioplasty, insertion of stents, catheters, grafts (including arterial and venous fistulas) and organ transplants) and unwanted post-surgical tissue or organ adhesions and scarring. The fibrosis can also be associated with increased cellular proliferation, for example, glomerular proliferative disease and vascular stiffness caused by cell proliferation, medial and intimal calcification. Other indications are associated with abnormal cellular proliferation, for example, cancer, particularly when growth or metastasis is related to upregulation of CCN2 expression, atherosclerosis, bone disease, osteophorosis, renal osteodystrophy, osteochondrodysplasia, osteitis fibrosa, osteoclastogenesis disease, vascular resistance, vascular calcification, tumorigenesis, and extracellular matrix disregulation. The pathology can be secondary to, the increased production/secretion and/or activity of TGF-β, wound healing, chronic kidney disease, intraglomerular hypertension, cancer cell growth, diabetes, inflammation, hyperglycemia, hypertension, renal proliferative disease, altered integrin receptor expression, extracellular matrix disregulation disease or connective tissue disease.

Results from a study of the effect of CCN3 peptides on the growth of human chronic myelogenous leukemia cells.

Another potential use of the methods described in the invention is for the treatment of cancers. CCN3 has been shown to play a role in limiting the growth of certain cancers. CCNp generated to mimic the effects of the function of CCN3 to prevent, reduce, stop or reverse progression of fibrosis/scarring may also serve to limit cancer growth. FIG. 12A shows a bar graph of cellular proliferation of human chronic myelogenous leukemia cells (K562) as percent of the growth of the untreated control. In untreated cells (Control) and those pre-incubated with quantities (approximately 10 nM) of a commercial recombinant CCN3 (rCCN3c), or full length CCN3 made in our laboratory, represented by several preparations rCCN3 8 (SEQ ID NO: 44), rCCN3 9 (SEQ ID NO: 44), rCCN3 10 (SEQ ID NO: 44), rCCN3 11 (SEQ ID NO: 44), or the peptides CCN p37 or CCN p38 were allowed to grow, then proliferation measured by the CellTiter-Glo®Luminescent Cell Viability Assay Control untreated cells, or cells (McCallum, L et al, *CCN3: a key growth regulator in Chronic Myeloid Leukaemia*, J Cell Commun Signal. 2009 Jun.; 3(2): 115-124.). The latter is a homogeneous method of determining the number of viable cells in culture based on quantitation of the ATP present, an indicator of metabolically active cells. Our results showed that the commercially produced full length CCN3 (SEQ. ID. NO: 67) produces an approximate 35% reduction in growth and/or viability over the period tested. In comparison, CCNp37 produces 15-20% inhibition and CCNp38 approximately 40% inhibition of cell growth. Thus the activity was greater than the full-length CCN3.

FIG. 12B shows the testing of CCNp37-1 (SEQ. ID. 37) and CCNp38-1 (SEQ. ID. 38) for their ability to inhibit the growth of chronic myelogenous leukemia cells (CML) in culture and a comparison to rCCN3 (SEQ. ID. 44). Both peptides were able to inhibit the growth of CML cells by slowing their replication time, and CCNp38-1 worked better than CCN3. Therefore, these CCNp peptides would be expected to be therapeutic in the treatment of CML, and other forms of cancer to reduce cell growth and to reduce metastasis.

Information on the role of CCN3 in cutaneous wound healing, including skin scarring, is largely unknown. We hypothesized that CCN3, primarily directed at CCN2, plays a critical regulatory role in the molecular and cellular events which underlie the wound healing response including scar formation/resolution. Further, we hypothesized that the ratio of CCN3/CCN2 is critical for the balance to optimal wound healing with minimization and/or reversal of scar formation. When suboptimal, endogenous regulation or exogenous treatment can be used to modulate remodeling of the ECM for improved healing/scarring. It was also possible but untested, that small peptide mimics of CCN3 could also improve wound healing and/or scarring in human skin. This would be effective in impaired healing, for example diabetic skin lesions, but would also be useful in minimizing scarring, for example post-surgery including face reconstruction, breast augmentation etc., in genetic-based severe scarring including keloids.

To test this we used a cell culture model of skin healing/scarring, which employed the use of primary human skin fibroblasts derived from foreskins collected post circumcision. These have been used extensively in the past to grown in culture and treated with agents that are known to drive wound healing and or scarring. We were also interested in a rare form of skin fibrosis/scarring that can lead to systemic disease and death known as nephrogenic systemic fibrosis (NSF). NSF is a complication of NMR diagnostics in renal impaired patients, where gadolinium (GAD), a heavy metal, is used as a contrast agent, but in some cases appears to deposit in skin. Although the mechanism for development of skin fibrosis and subsequent systemic disease is not yet completely understood, we have developed a model that has allowed elucidation of the probable pathway to skin fibrosis (Bhagavathula, N., M. K. Dame, M. DaSilva, W. Jenkins, M. N. Aslam, P. Perone and J. Varani (2010)). "Fibroblast response to gadolinium: role for platelet-derived growth factor receptor." Invest Radiol 45(12): 769-777). This disease is characterized as a hyperproliferative disease, and in our model it was shown that PDGF produced by resident skin fibroblasts are stimulated by GAD to increase their production of PDGF which acts to induce proliferation and the increased production of MMPs, regulators of ECM breakdown and thus turnover, including the major MMP, MMP-1. At the same time tissue inhibitors of MMPs (TIMPs) are also affected by exposure to GAD. Last, although, fibroblasts do not appear to produce TGF-beta in response to GAD, tissue macrophages, part of the local immune response, are stimulated by GAD to produce increased amounts of TGF-beta. It appears that local fibroblasts then respond to this increased TGF-beta by increasing their production of ECM, including predominantly collagen type 1.

We examined the role of CCN3 and CCNp in fibroproliferative/fibrotic responses in human dermal fibroblasts exposed to Omniscan, one of the gadolinium-based contrast agents associated with development of nephrogenic systemic fibrosis. These studies were carried out as we have previously described (Riser, B. L., N. Bhagavathula, P. Perone, K. Garchow, Y. Xu, G. J. Fisher, F. Najmabadi, D. Attili and J. Varani (2012)). "Gadolinium-induced fibrosis is counter-regulated by CCN3 in human dermal fibroblasts: a model for potential treatment of nephrogenic systemic fibrosis." J Cell Commun Signal 6(2): 97-105.). In our studies, human dermal fibroblasts were exposed to Omniscan; or to PDGF and TGF-β1 as controls. Cellular proliferation was assessed along with MMP-1 (by ELISA and gelatin zymography), TIMP-1 (by ELISA) and COL1 (by ELISA) in the absence and presence of CCN3 and CCNp. CCN3 and CCNp38 was added to cells at 10 nM concentration and at the same time as PDGF. In parallel, CCN3 production was assessed in control and Omniscan-treated cells. In most case the results shown (each bar) are the mean of 3-5 separate experiments, using fibroblasts from different donors. CCN3 was produced in our laboratory from the human embryonic kidney cell line (HEK-293) transfected with the complete human CCN3 gene, and producing an approximate 55 kDa, full-length CCN3 product. A second source of CCN3 was obtained from Pepro Tech Corporation (Rocky Hill, N.J.) and is produced in a prokaryote cell line.

FIG. 13 demonstrates the increased human skin fibroblast proliferation in response to Omniscan (GAD). FIG. 14 shows that human skin fibroblasts produce and secrete CCN3 in culture under basal conditions, and the exposure to GAD dose-dependently decreases this CCN3 production, while at the same time increasing cell proliferation (compare to FIG. 13). This suggested that CCN3 is able to control fibroblast proliferation. This is important since, NSF, and certain other fibrotic diseases are characterized as fibroproliferative diseases. In these instances proliferation of a key effecter cell results in the overaccumulation of ECM, i.e., collagen, and fibrosis.

Since it had been shown that skin fibroblasts also produce the cytokine platelet derived growth factor (PDGF) in response in response to GAD, and this is the likely mediator of the increased cell proliferation (Bhagavathula, N., M. K. Dame, M. DaSilva, W. Jenkins, M. N. Aslam, P. Perone and J. Varani (2010)). "Fibroblast response to gadolinium: role for platelet-derived growth factor receptor." Invest Radiol 45(12): 769-777), we looked next at the response to PDGF, and the role of CCN3 and CCNp. FIG. 15 demonstrates that human fibroblast proliferation is increased by PDGF and this stimulation is blocked by the addition of CCN3 protein and equally wellby CCNp38-3 (Seq. ID. No. 56). FIG. 16 shows that TGF-beta does not stimulate cell proliferation in this model, and neither CCN3 (SEQ. ID. No. 67) nor CCNp38-3 (Seq. ID. No. 56) has an effect on baseline cell growth.

Extracellular matrix (ECM) accumulation is a dynamic process made up of both regulated synthesis and breakdown (ECM turnover). Accumulation or overaccumulation in fibrosis is the result of an imbalance in the two and can therefore be the result of increased synthesis or decreased turnover rates. Fibrosis is often characterized by an increase in both synthesis and breakdown, i.e., increased turnover, and is the result of the net change. Matrix metalloproteinase one (MMP-1) acts to increase breakdown, whereas tissue inhibitors of MMP (e.g., TIMPs) at least in part to control the activity of MMP.

FIG. 17 shows that PDGF also acts to increase MMP-1 activity, whereas CCN3 is able to block that increase. CCNp38-3 (Seq. ID. No. 56) works better than CCN3 protein to accomplish this blockade. FIG. 18 shows no stimulating effect of TGF-beta and therefore no effect of CCN3 or the peptide.

FIG. 19 shows that PDGF also acts to increase TIMP-1 production and neither CCNp38-3 (Seq. ID. No. 56) nor CCN3 (SEQ. ID. No. 67) is able to block or reduce the increase in TIMP-1 production. FIG. 20 shows that TGF-beta1 fails to stimulate TIMP-1 production and neither CCNp38-3 nor CCN3 have an effect. FIG. 21 shows that TGF-beta exposure increases pro-collagen production 2-fold or greater and both CCN3 ((SEQ. ID. No. 67) and CCNp38-3 (Seq. ID. No. 56)) completely block the increase.

Collectively, these results show that CCN3 is an endogenous anti-scarring agent in the skin, and will therefore as shown be particularly important in NSF and likely other forms of skin scarring and in organs including the skin where there is exposure to other heavy metals. CCNp38-3 (SEQ. ID. 56) will also be useful to treat such disorders.

Next we created and tested for efficacy, additional CCNp including those with the cysteines intact (native sequence) from CCNp37 and CCNp38 and those that were modified by either shortening the peptide by 1 or 2 amino acids or lengthening by one amino acid. These agents were added to human skin fibroblasts in increasing concentrations from 1 nM to 100 nM and compared to the equal concentration of CCN3 (SEQ. ID. NO: 67). They were added just prior to the addition of either TGF-beta or PDGF, depending on the experiment.

FIGS. 22-24 show the test results of the effect of modifications in CCNp37 and CCNp38 (as described) on PDGF stimulated human fibroblast proliferation at 1 nM, 10 nM, and 100 nM concentrations respectively and compared the effect to that of CCN3, to determine their suitability as therapeutic agents.

FIG. 22 shows, human skin fibroblast proliferation in response to PDGF and the effect of 1 nM CCN3 or CCNp peptide. As expected PDGF exposure produced a strong increase in cell proliferation. CCN3 (SEQ. ID. No. 67) alone slightly decreased proliferation whereas all of the peptides had a similar or greater reduction (8-22%) in proliferation. FIG. 23 shows human skin fibroblast proliferation in response to PDGF and the effect of 10 nM CCN3 or CCNp peptide. CCN3 alone produced a 33% reduction in proliferation, whereas the CCNp peptides produced a similar 19-30% inhibition. FIG. 24 shows human skin fibroblast proliferation in response to PDGF and the effect of 100 nM CCN3 or CCNp peptides. CCN3 alone produced a 46% reduction in proliferation, whereas the CCNp peptides produced a similar 19-36% inhibition.

Taken as a whole there was a dose-dependent efficacy of CCN3 and all of the CCNp peptides in this tested group, although there were some differences in the CCNp peptides dependent on the modification. Adding an amino acid to the C-term end of CCNp 38 did not improve control of proliferation. Shortening CCNp38 at the N-term may have reduced slightly the ability to block proliferation. The native form of CCNp38 inhibited proliferation stimulated by PDGF, but was not as effective as the substituted form. CCNp37 shortened by 2 amino acids at the N or C-term produced cell proliferation-inhibition activity similar to the full 14 mer form. The native form of CCNp37 was active in inhibiting proliferation but was slightly less effective at most concentrations.

FIGS. 25-27 show the test results of the effect of modifications in CCNp37 and CCNp38 (as described) on their ability to block PDGF stimulated MMP-1 production, as a measure of their effectiveness in blocking skin fibrosis/scarring.

In FIG. 25, CCN3 at 1 nM was able to block little or no MMP-1 production, whereas all of the peptides tested in this series blocked significantly at 1 nM (16-44%). In FIG. 26, the effect of CCN3 at 10 nM was increased (to 27% reduction in MMP-1), whereas the CCNp peptides in some cases increased their activity to as much as 60% inhibition. In FIG. 27 at 100 nM CCN3 reached a 30% reduction in the stimulated MMP-1 production, whereas all CCNp peptides had similar or stronger activity, with CCNp38-3 and CCNp38-4 blocking up to about 60%. All peptide variants were able to block a marked level of MMP-1 production, including those with either cysteine intact or a replacement with serine. However, when CCNp37 had the native cysteine intact, or was made slightly shorter by reducing 2 amino acids at the N- or C-terminus, the ability to block MMP-1 production was reduced at all concentrations.

For CCNp38, the mouse sequence was effective, but slightly less effective in these human cells than the human sequence. The native CCNp38 produced similar activity to the cysteine substituted sequence. Reducing 2 amino acids from the N-term end or adding 1 amino acid to the C-term end resulted in slightly lower activity, but still produced inhibition of PDGF-stimulated MMP-1 production. Because MMP-1 production is important to ECM turnover, and other critical biological activities, the ability of these short peptides to modify its production can be interpreted to mean that they can be used as therapeutic agents in fibrosis, cancer and other pathologies where there is either a misregulation of MMP-1, or a need to block the production of MMP-1 involved in other disease, including inflammation.

FIGS. 28-30, show the test results of the same series of peptides for their ability to block PDGF stimulated TIMP-1 production, as a measure of their effectiveness to alter the accumulation of ECM and thus skin fibrosis/scarring, and other related disease. TIMP-1 production is known to be associated with a reduction in ECM breakdown and thus reduced turnover and in some cases increased ECM accumulation, including collagen. Increased turnover may also result in misstructured, or imperfect, lower functioning, ECM. We found that unlike the case for MMP-1, CCN3 was unable to block the increase in TIMP-1 stimulated by PDGF (FIGS. 29 and 30 [not tested in FIG. 28]). As was the case for CCN3, most of the peptides were also unable to alter the production of TIMP-1 even at the highest dose used. However, unexpectedly CCNp37-12 (Seq. ID. No. 37) and CCNp38-1 (Seq. ID. No. 38) produced approximately 50% and 70% reduction respectively in TIMP-1 (FIG. 30). CCNp38-3 (Seq. ID. No. 56), 38-4 (Seq. ID. No. 50), and 38-9 (Seq. ID. No. 57) were tested at the high dose only. These results demonstrate that the ability of CCNp peptides, and CCN3 to block the stimulated production of MMP-1 above (FIG. 25, 26, 27), was not likely due to their ability to increase TIMP-1. Since, in many pathologies, the ability to heal versus the inability to heal, and to form scar or fibrosis, is the result of the balance of ECM synthesis versus breakdown, the ability to therapeutically control this process by selectively treating with a CCN3, or specific CCNp peptide, and at the proper timing, to control synthesis versus breakdown, and thus the balance of turnover, will allow the prevention of progression as well as the reversal of pathology to normal tissue.

FIGS. 31-33 show the test results of the effect of modifications in CCNp37 and CCNp38 (as described) on TGF-beta-stimulated human fibroblast pro-collagen production and compared the effect to that of CCN3 (Seq. ID. No. 67), to determine suitability as therapeutic agents. As expected, TGF-beta significantly increased the production of pro-collagen type 1 whereas CCN3 was able to block from 66% to approximately 86% of the stimulated pro-collagen production as the dose was increased (1-100 nM). All of the peptides tested except CCNp 37-12 (Seq. ID. No. 37) were able to reduce the stimulation of pro-collagen type 1 production to some degree. CCNp38-3 (Seq. ID. No. 56) however, was as effective as CCN3 (SEQ. ID. No. 67).

Collectively, the results from FIGS. 31-33 demonstrate that CCN3 and CCNp described herein, can be used to prevent or modify the course of healing, scarring and fibrosis in skin in NSF and likely in other skin conditions where PDFG, TGF-beta, CCN2, MMP-1, TIMP-1, and collagen are involved. This is also therefore likely to be the case in other forms, and organs where impaired healing, fibrosis, or inflammation are involved. The selective use of CCN3 or the appropriate CCNp peptide can therefore be used, and "custom tailored" for the patient in need. This was a further unexpected discovery.

Results from DN Animal Model

In addition to the data shown in above examples, that demonstrated an ability of CCNp37 and CCNp38 (SEQ. ID. 37, 38, 49, 50) in cell models of renal disease, this confirmation was further sought in an animal model of human disease. FIG. 34 shows the method used to test efficacy of peptide CCNp38 in an animal model of diabetic renal disease. This was carried out using the BTBR Ob/Ob mouse strain that has a defective leptin receptor that results in increased appetite. As a result it rapidly gains weight over the control strain and becomes hyperglycemic at about one month of age, going on to develop renal disease resembling that in humans. This is regarded by some to be the rodent model best mirroring renal disease in humans as a complication of diabetes. Animals were treated with either rCCN3 (SEQ. ID. NO: 67) or CCNp38 (SEQ. ID. NO: 38) beginning at 9 weeks of age, when early renal disease has been documented. The disease was allowed to develop for 9 weeks, then treatment started. Mice were treated 3 times per week for 8 weeks. At 17 weeks, blood and urine were collected, and animals sacrificed with organ samples collected. The effect of treatment with either CCN3 (2 concentrations, 2 or 20× the circulating amounts) or mimic peptide (CCNp38, 2 concentrations, 20 or 200× the equivalent molar circulating concentration of CCN3) was tested. Assays to determine the effect of CCN3 or peptide on expression of target fibrosis genes and clinical pathology were determined using methods as previously described (Riser, Amer J Pathology 2009) and (McIntosh, L M, et al., Selective CCR2-targeted macrophage depletion ameliorates experimental mesangioproliferative glomerulonephritis, Clinical and Experimental Immunology, 2008, 155, 295-303).

FIG. 34 shows the method used to test efficacy of peptide CCNp38 in an animal model of diabetic renal disease. This was carried out using the BT/BR Ob/Ob mouse strain that has a defective leptin receptor that results in increased appetite. As a result mice rapidly gain weight over the control strain and become hyperglycemic at about one month of age going on to develop renal disease resembling that in humans. This is regarded by some to be the best rodent model for mirroring renal disease in humans as a complication of diabetes. The lower part of FIG. 34 shows the documented changes that occur in this mice strain, primarily focused on the kidney. The upper part of the figure shows the comparable changes that have been documented and are characteristic of human progression. Animals were treated with either rCCN3 (SEQ. ID. NO: 67) or CCNp38 (SEQ. ID. NO: 38) beginning at 9 weeks of age, when early renal disease has been documented. Mice were treated for 8 weeks, then sacrificed and measured for renal disease and other complications, and the effect drug treatment. Test animals were documented to have developed diabetes by 9 weeks, and were randomized for treatment, thus providing equivalent blood glucose levels in each treated group.

FIG. 35 shows that 17 weeks of diabetes elevates plasma creatinine, substantiating renal damage, and 8 weeks of treatment with CCN3 (SEQ. ID. NO: 67) or CCNp38 (SEQ. ID. 38), reduces or blocks this pathology. FIG. 36 shows that 17 weeks of diabetes elevates the albumin to creatinine ratio, substantiating protein leakage and renal damage, and 8 weeks of treatment with CCN3 or CCNp38 greatly blocks this pathology. FIGS. 37A and B shows that 17 weeks of diabetes results in mesangial expansion, substantiating renal fibrosis, and 8 weeks of treatment with CCN3 or CCNp38 greatly block this pathology and treats the disease. FIG. 37A shows qualitatively by PAS staining, in gray scale, that 17 weeks of diabetes results in mesangial expansion, substantiating renal fibrosis (white stain shows collagen deposition). FIG. 37B shows quantitatively by image analysis of multiple PAS stains (3 sections per mouse/7 mice per treatment group) that that 17 weeks of diabetes results in mesangial expansion, substantiating renal fibrosis., and 8 weeks of treatment with CCN3 or CCNp38 greatly blocks/treats this pathology.

FIG. 38 shows that renal mRNA levels for the fibrosis gene CCN2 are increased by diabetes, and treatment with CCN3 or CCNp38 greatly reduces or blocks the increase, thus treating the disease. FIG. 39 shows that renal mRNA levels for the fibrosis gene Col1A2 are increased by diabetes, and treatment with CCN3 or CCNp38 greatly reduces or blocks the increase, thus treating the disease. FIG. 40 shows that renal mRNA levels for the control 18S rRNA are not increased by diabetes, and treatment with CCN3 or CCNp38 has no effect on levels. These data demonstrate the usefulness of CCNp peptides in the treatment of renal fibrosis. They demonstrate a useful method and dose of treatment, however more or less frequent dosing and with higher or lower dose could be used depending on the individual patient needs and the route of delivery described in greater detail below.

A complication of diabetes, obesity, older age, alcohol use and other physiological abnormalities including metabolic syndrome is fatty liver. Accumulation of fat may also be accompanied by a progressive inflammation of the liver (hepatitis), called steatohepatitis. Fatty liver may be termed alcoholic steatosis or nonalcoholic fatty liver disease (NAFLD), and the more severe forms as alcoholic steatohepatitis and non-alcoholic steatohepatitis (NASH). In some cases this can lead to liver fibrosis or cirrhosis, one of the leading causes of death in diabetic patients. Liver cancer is rare, but does not appear to occur without first having liver fibrosis. CCN2 has been shown to be increased in liver fibrosis and liver cancer, and has been shown to be causal in certain animal models of liver fibrosis (Connective tissue growth factor (CCN2, CTGF) and organ fibrosis: lessons from transgenic animals, DR Brigstock—Journal of cell communication and signaling, 2010—Springer) (Connective tissue growth factor: a fibrogenic master switch in fibrotic liver disease, Olav A. Gressner, Axel M. Gressner, Liver International, first published online: 6 Aug. 2008, 1478-3231).

Since a common complication of diabetes is fatty liver, hepatitis, NASH, and in some cases liver fibrosis, we used the BTBR Ob/Ob mouse experiments described above as a model of human liver disease to examine the possibility that CCN3 or more particularly CCNp peptides might provide a treatment to prevent, treat, or reverse the liver disease described above.

FIG. 41 shows that liver weight is greatly increased by 13 weeks of obesity and diabetes, demonstrating steatosis. Treatment with for 8 weeks with CCN3 or CCNp38 slightly reduces this increase. FIG. 42 shows that liver mRNA levels for the fibrosis gene CCN2 are increased by diabetes, substantiating an inflammatory response and initiation of liver hepatitis/fibrosis. Treatment with CCNp38 dose-dependently reduced the increase. FIG. 44 shows that liver mRNA levels for the fibrosis gene Col1A2 are increased by diabetes, substantiating the initiation of fibrosis. Treatment with CCN3 or CCNp38 dose-dependently reduced, or blocked the increase in collagen expression. This demonstrates usefulness for CCN3, but more effectively, CCNp peptides for treating steatosis, hepatitis, liver fibrosis, and prevention of liver cancer.

A common type of cardiac disease is fibrosis. This can occur in the heart muscle itself, the valves of the heart, and/or the coronary arteries. It can be a slow progressive disease associated with inflammation and/or fatty diet, or can result from acute event including myocardial infarction (MI). It is a common complication of chronic kidney disease and diabetes. Another form of heart disease is cardiac hypertrophy. This can be associated with genetic alteration or can result from injury or overload to the heart and is also associated with fibrosis. CCN2 is upregulated and thought to be an important causal factor in the development of cardiac fibrosis and cardiac hypertrophy (Wang, Xiaoyu, et al. "Adverse effects of high glucose and free fatty acid on cardiomyocytes are mediated by connective tissue growth factor." *American Journal of Physiology-Cell Physiology* 297.6 (2009): C1490-C1500), (Connective tissue growth factor and cardiac fibrosis, A. Daniels[1], M. Van Bilsen[1], R. Goldschmeding[2], G. J. Van Der Vusse[1], F. A. Van Nieuwenhoven[1], Acta Physiologica Article first published online: 27 NOV 2008, 1748-1716).

A second important molecue in cardiac fibrosis is PAI. PAI-1 has been shown to be increased post MI and also following other forms of injury in the heart associated with fibrosis. Studies in PAI-1 deficient mice have shown that this deficiency protects against fibrosis (PAI-1 in Tissue Fibrosis, Asish K. Ghosh and Douglas E. Vaughan, J. Cell. Physiol. 227: 493-507, 2012.)

The BTBR Ob/Ob mouse was used to model human cardiac disease associated with diabetes and also chronic renal disease, to determine efficacy of CCN3 and CCNp peptides on the development of cardiac changes associated with diabetes, including cardiac fibrosis. We examined the heart from the same set of experiments as describe above for the kidney. FIG. 44 shows that heart mRNA levels for the fibrosis gene plasminogen activator inhibitor 1 (PAI-1) a target pro-fibrotic gene is increased by diabetes, substantiating the initiation of fibrosis. Treatment with CCNp38 greatly reduces, and at the high dose blocks the increase. Since CCNp has been shown to inhibit the production and activity of CCN2 and it has been shown here to block the increase in PAI-1 in the heart of diabetic mice associated with fibrosis, it can be used as a preventative or treatment for cardiac fibrosis, not limited to, but including those associated with diabetes, chronic kidney disease, atherosclerosis, vascular calcification, and hypertrophy. This can be further proven, for example by using a mouse model of familial hypertrophic cardiomyopathy (Severe Heart Failure and Early Mortality in a Double-Mutation Mouse Model of Familial Hypertrophic Cardiomyopathy, Tatiana Tsoutsman, Matthew Kelly, Dominic C. H. Ng, PhD; Ju-En Tan, Emily Tu, Lien Lam, Marie A. Bogoyevitch, Christine E. Seidman, J. G. Seidman, Christopher Semsarian, *Circulation.* 2008; 117:1820-1831). In this case, CCN3 or CCNp peptides would be administered beginning at birth, by preferably IV, IP or another route. In some groups, the agent described would be administered shortly after the established development of cardiac hypertrophy. Treatment could be extended to about 21 days, then heart collected and examined for reduction in cardiac pathology (including measurement by histopathology). Measurements of dilated cardiomyopathy and heart failure, and level of ventricular arrhythmias, and blood biomarkers of cardiac disease would also be run to demonstrate efficacy of the agent. In one set of experiments the end point measured would be reduction in mortality.

Sustained neuroinflammation strongly contributes to the pathogenesis of pain. The clinical challenge of chronic pain relief has demonstrated a role for molecules including CCN3 and MMP-1 among others. It has recently been shown that CCN3 is a modulator of these inflammatory mediators in a preclinical model of persistent inflammatory pain. They showed that in this model that injury with neuroinflammation results in the downregulation of CCN3 in nerves. Intrathecal treatment specifically abolished the induction of MMP-2 and other modulators of inflammation and pain in rats. This inhibitory effect on MMP is associated with reduced pain on mechanical stimulation (NOV/CCN3 attenuates inflammatory pain through regulation of matrix metalloproteinases-2 and -9, Lara Kular, Cyril Rivat, Brigitte Lelongt, Claire Calmel, Maryvonne Laurent, Michel Pohl, Patrick Kitabgi, Stéphane Melik-Parsadaniantz and Cécile Martinerie. Journal of Neuroinflammation, 2012, 9:36). Accordingly, since CCNp peptides described herein have been demonstrated to mimic the ability of CCN3, and to reduce stimulated MMP production, then CCNp37 and CCnp38 and their variants can be used to treat neuroinflammation and pain. This could be further proven in two types of experiments the first in rats to which Freund's adjuvant (CFA) is given to induce a model of persistent inflammatory pain (same reference as above). CCNp37 and CCNp38 and combinations would then be administered intrathecally or other, beginning before the CFA, to show efficacy for prevention, or beginning after developed neuroinflammation to demonstrate efficacy of treatment. The second method would use cultured primary sensory neurons for in vitro experiments (same reference) and CCNp peptides tested to show an ability to block IL-1b- and TNF-a-induced MMP-2, MMP-9 and CCL2 expression, as a model for human neuroinflammation and pain.

As an additional aspect, the invention includes kits which comprise one or more pharmaceutical formulations for administration of CCN3 peptides to a patient packaged in a manner which facilitates their use for administration to subjects. In one embodiment, such a kit includes pharmaceutical formulation described herein (e.g., a composition comprising a CCN3 protein or a CCNp peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none). In one embodiment, the kit contains a first container having the CCNp peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

The present invention further provides administering the CCNp peptides to a human subject through a route of administration including intravenous, intramuscular, nasal, topical, vaginal, anal, transdermal, inhalation, oral, bucal, intraperitoneal, intraosseous and combinations of the same. The transdermal route of administration includes transdermal patch or transdermal electrophoresis. It should also be understood that the CCNp peptide can be modified by attaching a carrier molecule or entity, as is well known in the art, to protect the peptide from degradation, to target the peptide to a desired location in the human, and to control the rate of delivery. Suitable carrier molecules include, but are not limited to, glycol groups, polyethylene glycol (PEG), proteins, including serum proteins. The present invention contemplates using excipients that are used in the pharmaceutical industry for the prescribed routes of delivery set forth above. The present invention contemplates modifying the CCN3 peptide to increase its stability, shelf life, half-life in vivo, targeting within the body, to improve its attachment to a cell of interest or entry into the cell of interest.

In one preferred form of the invention, the CCNp peptides can be used in stem cell treatment formulations by adding the peptides to cord blood, or bone marrow isolates to generate therapeutic stem cells ex vivo. Also, it could be speculated that such treatment in vivo might enhance the activity of naturally occurring stem cells, for better recovery from serious injury including ischemic heart disease, fibrosis, heart and liver failure among others. Hematopoietic stem cells (HSC) would be obtained from a patient (or donor) e.g., including bone marrow, peripheral blood, and umbilical cord blood cells, including autologous (marrow or PBSC) or allogeneic (HLA-matched related [MRD], HLA-matched unrelated [MUD], mismatched related or unrelated donors, and umbilical cord blood [UCB] or form an established stem cell line). These stem cells would then be incubated for a period of time in the presence of CCN3 or CCNp peptides, described herein, to allow growth (expansion of numbers) and/or differentiation to the needed cell type or form. The conditioned stem cell would then be delivered to a patient, e.g., IV or other route of administration described herein, with a given pathology including but not limited to fibrosis, cancer, multiple sclerosis, cystic fibrosis in order to target to the site of injury and pathology. The conditioned stem cells would serve to: 1) replace specifically injured or dead cells at the site of pathology (e.g. cardiac muscle cells, kidney mesangial cells, liver stellate cells) and 2) to provide accessory cells differentiated and capable of releasing cytokines and other factors necessary for repair or replacement.

The present invention provides for delivering an effective amount of the CCN3 peptides which can be determined by methods such as dose titration or other techniques known to those skilled in the art and can include dosages within the range of 0.1 nanomolar to 1 micromolar or approximately 0.1 nanogram per milliter to 1 microgram per milliliter. Concentrated amounts may also be required depending on the delivery form used.

The practice of the present invention will employ and incorporate, unless otherwise indicated, conventional techniques of cell biology, cell culture, molecular biology, microbiology, genetic engineering and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

The invention claimed is:

1. A method for treating a human patient with fatty liver disease, steatosis, hepatitis, or neural inflammation comprising:

administering to the subj ect an effective amount of an agent selected from the group consisting of SEQ ID NOs: 48-50, 52, and 63 or combinations thereof.

2. The method of claim 1 wherein the step of administering comprises delivering through a route of administration selected from the group consisting of intravenous, intramuscular, nasal, topical, vaginal, anal, transdermal, inhalation, oral, buccal, intraperitoneal, intrathecal, intraosseous and combinations thereof.

3. The method of claim 2 wherein the transdermal route of administration includes transdermal patch or transdermal electrophoresis.

4. The method of claim 1 further comprising the step of modifying the agent to increase its stability, shelf life, half-life, in vivo targeting, or to improve its attachment to a cell of interest, or entry into the cell of interest.

5. A method for treating fatty liver disease, steatosis, liver fibrosis, or liver cancer in a subject in need thereof comprising administering to the subject an effective amount of an analog CCNp38 peptide fragment with native cysteine residues substituted with a replacement amino acid.

6. The method of claim 5 wherein the replacement amino acid is selected from the group consisting of serine, alanine, glycine, S-methylated cysteine or a combination thereof.

7. The method of claim 6 wherein the replacement amino acid is serine.

8. The method of claim 5 wherein the step of administering comprises delivering through a route of administration selected from the group consisting of intravenous, intramuscular, nasal, topical, vaginal, anal, transdermal, inhalation, oral, buccal, intraperitoneal, intraosseous and combinations of the same.

9. The method of claim 8 wherein the transdermal route of administration includes transdermal patch or transdermal electrophoresis.

10. The method of claim 5 wherein the CCNp38 peptide fragment is modified by a carrier molecule.

11. The method of claim 10 wherein the carrier molecule is selected from the group consisting of polyethylene glycol (PEG), glycol groups, proteins, and serum proteins.

12. The method of claim 5 further comprising the step of modifying the CCNp38 peptide fragment to increase its stability, shelf life, half-life, in vivo targeting, or to improve its attachment to a cell of interest, or entry into the cell of interest.

13. The method of claim 5, wherein the step of administering comprises delivering the analog CCNp38 peptide in a stem cell solution.

* * * * *

```
                              SEQUENCE LISTING

<160> NUMBER OF SEQ ID NOS: 67

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ser Leu Phe Leu Arg Lys Arg Ser Leu Ser Leu Gly Phe Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Leu Gly Phe Leu Leu Phe His Leu Leu Ser Gln Val Ser Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gln Val Ser Ala Ser Leu Arg Ser Pro Ser Arg Ser Pro Pro
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Pro Ser Arg Ser Pro Pro Lys Ser Pro Ser Ile Ser Pro Thr
1               5                   10                  15

Ser Ala

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Pro Thr Ser Ala Pro Gly Val Arg Ser Val Leu Asp Gly Ser
1               5                   10                  15
```

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Leu Asp Gly Ser Ser Ser Ser Pro Val Ser Ala Arg Gln Arg
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ala Arg Gln Arg Gly Glu Ser Ser Ser Glu Met Arg Pro Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Met Arg Pro Ser Asp Gln Ser Ser Gly Leu Tyr Ser Asp Arg
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Tyr Ser Asp Arg Ser Ala Asp Pro Asn Asn Gln Thr Gly Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Gln Thr Gly Ile Ser Met Val Pro Glu Gly Asp Asn Ser Val
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 11

Gly Asp Asn Ser Val Phe Asp Gly Val Ile Tyr Arg Asn Gly Glu
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Arg Asn Gly Glu Lys Phe Glu Pro Asn Ser Gln Tyr Phe
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Tyr Phe Ser Thr Ser Arg Asp Gly Gln Ile Gly Ser Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ile Gly Ser Leu Pro Arg Ser Gln Leu Asp Val Leu Leu Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Val Leu Leu Pro Gly Pro Asp Ser Pro Ala Pro Arg Lys Val
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Pro Arg Lys Val Ala Val Pro Gly Glu Ser Ser Glu Lys
1               5                   10

<210> SEQ ID NO 17
<211> LENGTH: 17

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ser Glu Lys Trp Thr Ser Gly Ser Asp Glu Gln Gly Thr Gln Gly
1               5                   10                  15

Thr

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Glu Gln Gly Thr Gln Gly Thr Leu Gly Gly Leu Ala Leu Pro
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ala Leu Pro Ala Tyr Arg Pro Glu Ala Thr Val Gly Val
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Thr Val Gly Val Glu Val Ser Asp Ser Ser Ile Asn Ser Ile
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ile Asn Ser Ile Glu Gln Thr Thr Glu Trp Ser Ala Ser Ser
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Trp Ser Ala Ser Ser Lys Ser Gly Met Gly Val Ser Thr Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Ser Thr Arg Val Thr Asn Arg Asn Arg Gln Ser Glu Met
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Gln Ser Glu Met Val Lys Gln Thr Arg Leu Ser Ile Val Arg
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Ser Ile Val Arg Pro Ser Glu Gln Glu Pro Glu Glu Val Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Glu Glu Val Thr Asp Lys Lys Gly Lys Lys Ser Leu Arg Thr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ser Leu Arg Thr Lys Lys Ser Leu Lys Ala Ile His Leu Gln
1               5                   10                  15

<210> SEQ ID NO 28
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 28

Ala Ile His Leu Gln Phe Glu Asn Ser Thr Ser Leu Tyr Thr Tyr
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Leu Tyr Thr Tyr Lys Pro Arg Phe Ser Gly Val Ser Ser Asp
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Val Ser Ser Asp Gly Arg Ser Ser Thr Pro His Asn Thr Lys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro His Asn Thr Lys Thr Ile Gln Val Glu Phe Gln Ser Leu Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Gln Ser Leu Pro Gly Glu Ile Ile Lys Lys Pro Val Met Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Pro Val Met Val Ile Gly Thr Ser Thr Ser Tyr Ser Asn Ser
1               5                   10                  15
```

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Asn Ser Pro Gln Asn Asn Glu Ala Phe Leu Gln Asp Leu
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Phe Leu Gln Asp Leu Glu Leu Lys Thr Ser Arg Gly Glu Ile
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Gln Thr Arg Leu Ser Ile Val Arg Pro Ser Glu Gln
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Ser Gly Val Ser Ser Asp Gly Arg Ser Ser Thr Pro His
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Asp Arg Ser Ala Asp Pro Asn Asn Gln Thr Gly Ile Ser
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 39

Gln Thr Thr Glu Trp Ser Ala Ser Ser Lys Ser Ser Gly Met Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Ser Lys Ser Ser Gly Met Gly Val Ser Thr Arg Val Thr Asn
1               5                   10                  15

<210> SEQ ID NO 41
<211> LENGTH: 354
<212> TYPE: PRT
<213> ORGANISM: Mus sp.

<400> SEQUENCE: 41

Met Ser Leu Phe Leu Arg Lys Arg Cys Leu Cys Leu Gly Phe Leu Leu
1               5                   10                  15

Phe His Leu Leu Ser Gln Val Ser Ala Ser Leu Arg Cys Pro Ser Arg
                20                  25                  30

Cys Pro Pro Lys Cys Pro Ser Ile Ser Pro Thr Cys Ala Pro Gly Val
            35                  40                  45

Arg Ser Val Leu Asp Gly Cys Ser Cys Cys Pro Val Cys Ala Arg Gln
        50                  55                  60

Arg Gly Glu Ser Cys Ser Glu Met Arg Pro Cys Asp Gln Ser Ser Gly
65                  70                  75                  80

Leu Tyr Cys Asp Arg Ser Ala Asp Pro Asn Asn Gln Thr Gly Ile Cys
                85                  90                  95

Met Val Pro Glu Gly Asp Asn Cys Val Phe Asp Gly Val Ile Tyr Arg
            100                 105                 110

Asn Gly Glu Lys Phe Glu Pro Asn Cys Gln Tyr Phe Cys Thr Cys Arg
        115                 120                 125

Asp Gly Gln Ile Gly Cys Leu Pro Arg Cys Gln Leu Asp Val Leu Leu
    130                 135                 140

Pro Gly Pro Asp Cys Pro Ala Pro Arg Lys Val Ala Val Pro Gly Glu
145                 150                 155                 160

Cys Cys Glu Lys Trp Thr Cys Gly Ser Asp Glu Gln Gly Thr Gln Gly
                165                 170                 175

Thr Leu Gly Gly Leu Ala Leu Pro Ala Tyr Arg Pro Glu Ala Thr Val
            180                 185                 190

Gly Val Glu Val Ser Asp Ser Ser Ile Asn Cys Ile Glu Gln Thr Thr
        195                 200                 205

Glu Trp Ser Ala Cys Ser Lys Ser Cys Gly Met Gly Val Ser Thr Arg
    210                 215                 220

Val Thr Asn Arg Asn Arg Gln Cys Glu Met Val Lys Gln Thr Arg Leu
225                 230                 235                 240

Cys Ile Val Arg Pro Cys Glu Gln Glu Pro Glu Val Thr Asp Lys
                245                 250                 255

Lys Gly Lys Lys Cys Leu Arg Thr Lys Lys Ser Leu Lys Ala Ile His
            260                 265                 270

Leu Gln Phe Glu Asn Cys Thr Ser Leu Tyr Thr Tyr Lys Pro Arg Phe
```

```
            275                 280                 285
Cys Gly Val Cys Ser Asp Gly Arg Cys Cys Thr Pro His Asn Thr Lys
    290                 295                 300

Thr Ile Gln Val Glu Phe Gln Cys Leu Pro Gly Glu Ile Ile Lys Lys
305                 310                 315                 320

Pro Val Met Val Ile Gly Thr Cys Thr Cys Tyr Ser Asn Cys Pro Gln
                325                 330                 335

Asn Asn Glu Ala Phe Leu Gln Asp Leu Glu Leu Lys Thr Ser Arg Gly
            340                 345                 350

Glu Ile

<210> SEQ ID NO 42
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ser Leu Phe Leu Arg Lys Arg Ser Leu Ser Leu Gly Phe Leu Leu
1               5                   10                  15

Phe His Leu Leu Ser Gln Val Ser Ala Ser Leu Arg Ser Pro Ser Arg
            20                  25                  30

Ser Pro Pro Lys Ser Pro Ser Ile Ser Pro Thr Ser Ala Pro Gly Val
        35                  40                  45

Arg Ser Val Leu Asp Gly Ser Ser Ser Pro Val Ser Ala Arg Gln
    50                  55                  60

Arg Gly Glu Ser Ser Ser Glu Met Arg Pro Ser Asp Gln Ser Ser Gly
65                  70                  75                  80

Leu Tyr Ser Asp Arg Ser Ala Asp Pro Asn Asn Gln Thr Gly Ile Ser
                85                  90                  95

Met Val Pro Glu Gly Asp Asn Ser Val Phe Asp Gly Val Ile Tyr Arg
            100                 105                 110

Asn Gly Glu Lys Phe Glu Pro Asn Ser Gln Tyr Phe Ser Thr Ser Arg
        115                 120                 125

Asp Gly Gln Ile Gly Ser Leu Pro Arg Ser Gln Leu Asp Val Leu Leu
    130                 135                 140

Pro Gly Pro Asp Ser Pro Ala Pro Arg Lys Val Ala Val Pro Gly Glu
145                 150                 155                 160

Ser Ser Glu Lys Trp Thr Ser Gly Ser Asp Glu Gln Gly Thr Gln Gly
                165                 170                 175

Thr Leu Gly Gly Leu Ala Leu Pro Ala Tyr Arg Pro Glu Ala Thr Val
            180                 185                 190

Gly Val Glu Val Ser Asp Ser Ser Ile Asn Ser Ile Glu Gln Thr Thr
        195                 200                 205

Glu Trp Ser Ala Ser Ser Lys Ser Ser Gly Met Gly Val Ser Thr Arg
    210                 215                 220

Val Thr Asn Arg Asn Arg Gln Ser Glu Met Val Lys Gln Thr Arg Leu
225                 230                 235                 240

Ser Ile Val Arg Pro Ser Glu Gln Glu Pro Glu Val Thr Asp Lys
                245                 250                 255

Lys Gly Lys Lys Ser Leu Arg Thr Lys Lys Ser Leu Lys Ala Ile His
            260                 265                 270

Leu Gln Phe Glu Asn Ser Thr Ser Leu Tyr Thr Tyr Lys Pro Arg Phe
```

```
            275                 280                 285
Ser Gly Val Ser Ser Asp Gly Arg Ser Ser Thr Pro His Asn Thr Lys
    290                 295                 300

Thr Ile Gln Val Glu Phe Gln Ser Leu Pro Gly Glu Ile Ile Lys Lys
305                 310                 315                 320

Pro Val Met Val Ile Gly Thr Ser Thr Ser Tyr Ser Asn Ser Pro Gln
                325                 330                 335

Asn Asn Glu Ala Phe Leu Gln Asp Leu Glu Leu Lys Thr Ser Arg Gly
                340                 345                 350

Glu Ile

<210> SEQ ID NO 43
<211> LENGTH: 322
<212> TYPE: PRT
<213> ORGANISM: Homo sapiens

<400> SEQUENCE: 43

Val Leu Leu Ala Leu Cys Ser Arg Pro Ala Val Gly Gln Asn Cys Ser
1               5                   10                  15

Gly Pro Cys Arg Cys Pro Asp Glu Pro Ala Pro Arg Cys Pro Ala Gly
            20                  25                  30

Val Ser Leu Val Leu Asp Gly Cys Gly Cys Cys Arg Val Cys Ala Lys
        35                  40                  45

Gln Leu Gly Glu Leu Cys Thr Glu Arg Asp Pro Cys Asp Pro His Lys
    50                  55                  60

Gly Leu Phe Cys Asp Phe Gly Ser Pro Ala Asn Arg Lys Ile Gly Val
65                  70                  75                  80

Cys Thr Ala Lys Asp Gly Ala Pro Cys Ile Phe Gly Gly Thr Val Tyr
                85                  90                  95

Arg Ser Gly Glu Ser Phe Gln Ser Ser Cys Lys Tyr Gln Cys Thr Cys
            100                 105                 110

Leu Asp Gly Ala Val Gly Cys Met Pro Leu Cys Ser Met Asp Val Arg
        115                 120                 125

Leu Pro Ser Pro Asp Cys Pro Phe Pro Arg Arg Val Lys Leu Pro Gly
    130                 135                 140

Lys Cys Cys Glu Glu Trp Val Cys Asp Glu Pro Lys Asp Gln Thr Val
145                 150                 155                 160

Val Gly Pro Ala Leu Ala Ala Tyr Arg Leu Glu Asp Thr Phe Gly Pro
                165                 170                 175

Asp Pro Thr Met Ile Arg Ala Asn Cys Leu Val Gln Thr Thr Glu Trp
            180                 185                 190

Ser Ala Cys Ser Lys Thr Cys Gly Met Gly Ile Ser Thr Arg Val Thr
        195                 200                 205

Asn Asp Asn Ala Ser Cys Arg Leu Glu Lys Gln Ser Arg Leu Cys Met
    210                 215                 220

Val Arg Pro Cys Glu Ala Asp Leu Glu Glu Asn Ile Lys Lys Gly Lys
225                 230                 235                 240

Lys Cys Ile Arg Thr Pro Lys Ile Ser Lys Pro Ile Lys Phe Glu Leu
                245                 250                 255

Ser Gly Cys Thr Ser Met Lys Thr Tyr Arg Ala Lys Phe Cys Gly Val
            260                 265                 270

Cys Thr Asp Gly Arg Cys Cys Thr Pro His Arg Thr Thr Thr Leu Pro
        275                 280                 285

Val Glu Phe Lys Cys Pro Asp Gly Glu Val Met Lys Lys Asn Met Met
```

```
            290                 295                 300
Phe Ile Lys Thr Cys Ala Cys His Tyr Asn Cys Pro Gly Asp Asn Asp
305                 310                 315                 320

Ile Phe

<210> SEQ ID NO 44
<211> LENGTH: 324
<212> TYPE: PRT
<213> ORGANISM: Homo sapiens

<400> SEQUENCE: 44

Leu Leu Leu His Leu Leu Gly Gln Val Ala Ala Thr Gln Arg Cys Pro
1               5                   10                  15

Pro Gln Cys Pro Gly Arg Cys Pro Ala Thr Pro Thr Cys Ala Pro
            20                  25                  30

Gly Val Arg Ala Val Leu Asp Gly Cys Ser Cys Cys Leu Val Cys Ala
        35                  40                  45

Arg Gln Arg Gly Glu Ser Cys Ser Asp Leu Glu Pro Cys Asp Glu Ser
    50                  55                  60

Ser Gly Leu Tyr Cys Asp Arg Ser Ala Asp Pro Ser Asn Gln Thr Gly
65                  70                  75                  80

Ile Cys Thr Ala Val Glu Gly Asp Asn Cys Val Phe Asp Gly Val Ile
                85                  90                  95

Tyr Arg Ser Gly Glu Lys Phe Gln Pro Ser Cys Lys Phe Gln Cys Thr
            100                 105                 110

Cys Arg Asp Gly Gln Ile Gly Cys Val Pro Arg Cys Gln Leu Asp Val
        115                 120                 125

Leu Leu Pro Glu Pro Asn Cys Pro Ala Pro Arg Lys Val Glu Val Pro
    130                 135                 140

Gly Glu Cys Cys Glu Lys Trp Ile Cys Gly Pro Asp Glu Glu Asp Ser
145                 150                 155                 160

Leu Gly Gly Leu Thr Leu Ala Ala Tyr Arg Pro Glu Ala Thr Leu Gly
                165                 170                 175

Val Glu Val Ser Asp Ser Ser Val Asn Cys Ile Glu Gln Thr Thr Glu
            180                 185                 190

Trp Thr Ala Cys Ser Lys Ser Cys Gly Met Gly Phe Ser Thr Arg Val
        195                 200                 205

Thr Asn Arg Asn Arg Gln Cys Glu Met Leu Lys Gln Thr Arg Leu Cys
    210                 215                 220

Met Val Arg Pro Cys Glu Gln Glu Pro Glu Gln Pro Thr Asp Lys Lys
225                 230                 235                 240

Gly Lys Lys Cys Leu Arg Thr Lys Lys Ser Leu Lys Ala Ile His Leu
                245                 250                 255

Gln Phe Lys Asn Cys Thr Ser Leu His Thr Tyr Lys Pro Arg Phe Cys
            260                 265                 270

Gly Val Cys Ser Asp Gly Arg Cys Cys Thr Pro His Asn Thr Lys Thr
        275                 280                 285

Ile Gln Ala Glu Phe Gln Cys Ser Pro Gly Gln Ile Val Lys Lys Pro
    290                 295                 300

Val Met Val Ile Gly Thr Cys Thr Cys His Thr Asn Cys Pro Lys Asn
305                 310                 315                 320

Asn Glu Ala Phe

<210> SEQ ID NO 45
```

```
<211> LENGTH: 14
<212> TYPE: PRT
<213> ORGANISM: Mus sp.

<400> SEQUENCE: 45

Gln Thr Thr Glu Trp Ser Ala Cys Ser Lys Ser Cys Gly Met
1               5                   10

<210> SEQ ID NO 46
<211> LENGTH: 15
<212> TYPE: PRT
<213> ORGANISM: Mus sp.

<400> SEQUENCE: 46

Cys Ser Lys Ser Cys Gly Met Gly Val Ser Thr Arg Val Thr Asn
1               5                   10                  15

<210> SEQ ID NO 47
<211> LENGTH: 13
<212> TYPE: PRT
<213> ORGANISM: Mus sp.

<400> SEQUENCE: 47

Lys Gln Thr Arg Leu Cys Ile Val Arg Pro Cys Glu Gln
1               5                   10

<210> SEQ ID NO 48
<211> LENGTH: 14
<212> TYPE: PRT
<213> ORGANISM: Mus sp.

<400> SEQUENCE: 48

Phe Cys Gly Val Cys Ser Asp Gly Arg Cys Cys Thr Pro His
1               5                   10

<210> SEQ ID NO 49
<211> LENGTH: 14
<212> TYPE: PRT
<213> ORGANISM: Mus sp.

<400> SEQUENCE: 49

Cys Asp Arg Ser Ala Asp Pro Asn Asn Gln Thr Gly Ile Cys
1               5                   10

<210> SEQ ID NO 50
<211> LENGTH: 14
<212> TYPE: PRT
<213> ORGANISM: Homo sapiens

<400> SEQUENCE: 50

Cys Asp Arg Ser Ala Asp Pro Ser Asn Gln Thr Gly Ile Cys
1               5                   10

<210> SEQ ID NO 51
<211> LENGTH: 14
<212> TYPE: PRT
<213> ORGANISM: Homo sapiens

<400> SEQUENCE: 51

Phe Cys Gly Val Cys Thr Asp Gly Arg Cys Cys Thr Pro His
1               5                   10

<210> SEQ ID NO 52
<211> LENGTH: 14
<212> TYPE: PRT
```

<213> ORGANISM: Rattus sp.

<400> SEQUENCE: 52

Cys Asp Arg Ser Ala Asp Pro Asn Asn Glu Thr Gly Ile Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Asp Arg Ser Ala Asp Pro Asn Asn Glu Thr Gly Ile Ser
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Val Ser Ser Asp Gly Arg Ser Ser Thr Pro His
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Ser Gly Val Ser Ser Asp Gly Arg Ser Ser Thr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Asp Arg Ser Ala Asp Pro Ser Asn Gln Thr Gly Ile Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Ala Asp Pro Ser Asn Gln Thr Gly Ile Ser
1               5                   10

<210> SEQ ID NO 58

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Asp Arg Ser Ala Asp Pro Ser Asn Gln Thr Gly Ile Ser Thr
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Ala Asp Pro Asn Asn Gln Thr Gly Ile Ser
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ser Ala Asp Pro Asn Asn Glu Thr Gly Ile Ser
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Asp Arg Ser Ala Asp Pro Ser Asn Glu Thr Gly Ile Ser Thr
1               5                   10                  15

<210> SEQ ID NO 62
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Leu Leu His Leu Leu Gly Gln Val Ala Ala Thr Gln Arg Ser Pro
1               5                   10                  15

Pro Gln Ser Pro Gly Arg Ser Pro Ala Thr Pro Pro Thr Ser Ala Pro
                20                  25                  30

Gly Val Arg Ala Val Leu Asp Gly Ser Ser Ser Leu Val Ser Ala
            35                  40                  45

Arg Gln Arg Gly Glu Ser Ser Ser Asp Leu Glu Pro Ser Asp Glu Ser
        50                  55                  60

Ser Gly Leu Tyr Ser Asp Arg Ser Ala Asp Pro Ser Asn Gln Thr Gly
65                  70                  75                  80
```

```
Ile Ser Thr Ala Val Glu Gly Asp Asn Ser Phe Asp Gly Val Ile
                85                  90                  95

Tyr Arg Ser Gly Glu Lys Phe Gln Pro Ser Ser Lys Phe Gln Ser Thr
                100                 105                 110

Ser Arg Asp Gly Gln Ile Gly Ser Val Pro Arg Ser Gln Leu Asp Val
                115                 120                 125

Leu Leu Pro Glu Pro Asn Ser Pro Ala Pro Arg Lys Val Glu Val Pro
            130                 135                 140

Gly Glu Ser Ser Glu Lys Trp Ile Ser Gly Pro Asp Glu Glu Asp Ser
145                 150                 155                 160

Leu Gly Gly Leu Thr Leu Ala Ala Tyr Arg Pro Glu Ala Thr Leu Gly
                165                 170                 175

Val Glu Val Ser Asp Ser Ser Val Asn Ser Ile Glu Gln Thr Thr Glu
                180                 185                 190

Trp Thr Ala Ser Ser Lys Ser Ser Gly Met Gly Phe Ser Thr Arg Val
                195                 200                 205

Thr Asn Arg Asn Arg Gln Ser Glu Met Leu Lys Gln Thr Arg Leu Ser
            210                 215                 220

Met Val Arg Pro Ser Glu Gln Glu Pro Glu Gln Pro Thr Asp Lys Lys
225                 230                 235                 240

Gly Lys Lys Ser Leu Arg Thr Lys Lys Ser Leu Lys Ala Ile His Leu
                245                 250                 255

Gln Phe Lys Asn Ser Thr Ser Leu His Thr Tyr Lys Pro Arg Phe Ser
                260                 265                 270

Gly Val Ser Ser Asp Gly Arg Ser Ser Thr Pro His Asn Thr Lys Thr
            275                 280                 285

Ile Gln Ala Glu Phe Gln Ser Ser Pro Gly Gln Ile Val Lys Lys Pro
290                 295                 300

Val Met Val Ile Gly Thr Ser Thr Ser His Thr Asn Ser Pro Lys Asn
305                 310                 315                 320

Asn Glu Ala Phe

<210> SEQ ID NO 63
<211> LENGTH: 14
<212> TYPE: PRT
<213> ORGANISM: Homo sapiens

<400> SEQUENCE: 63

Phe Cys Gly Val Cys Ser Asp Gly Arg Cys Cys Thr Pro His
1               5                   10

<210> SEQ ID NO 64
<211> LENGTH: 14
<212> TYPE: PRT
<213> ORGANISM: Homo sapiens

<400> SEQUENCE: 64

Cys Asp Phe Gly Ser Pro Ala Asn Arg Lys Ile Gly Val Cys
1               5                   10

<210> SEQ ID NO 65
<211> LENGTH: 14
<212> TYPE: PRT
<213> ORGANISM: Mus sp.

<400> SEQUENCE: 65

Phe Cys Gly Val Cys Thr Asp Gly Arg Cys Cys Thr Pro His
```

<210> SEQ ID NO 66
<211> LENGTH: 14
<212> TYPE: PRT
<213> ORGANISM: Mus sp.

<400> SEQUENCE: 66

Cys Asp Phe Gly Ser Pro Ala Asn Arg Lys Ile Gly Val Cys
1               5                   10

<210> SEQ ID NO 67
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Gln Val Ala Ala Thr Gln Arg Cys Pro Gln Cys Pro Gly Arg
1               5                   10                  15

Cys Pro Ala Thr Pro Pro Thr Cys Ala Pro Gly Val Arg Ala Val Leu
                20                  25                  30

Asp Gly Cys Ser Cys Cys Leu Val Cys Ala Arg Gln Arg Gly Glu Ser
            35                  40                  45

Cys Ser Asp Leu Glu Pro Cys Asp Glu Ser Ser Gly Leu Tyr Cys Asp
        50                  55                  60

Arg Ser Ala Asp Pro Ser Asn Gln Thr Gly Ile Cys Thr Ala Val Glu
65                  70                  75                  80

Gly Asp Asn Cys Val Phe Asp Gly Val Ile Tyr Arg Ser Gly Glu Lys
                85                  90                  95

Phe Gln Pro Ser Cys Lys Phe Gln Cys Thr Cys Arg Asp Gly Gln Ile
            100                 105                 110

Gly Cys Val Pro Arg Cys Gln Leu Asp Val Leu Leu Pro Glu Pro Asn
        115                 120                 125

Cys Pro Ala Pro Arg Lys Val Glu Val Pro Gly Glu Cys Cys Glu Lys
    130                 135                 140

Trp Ile Cys Gly Pro Asp Glu Glu Asp Ser Leu Gly Gly Leu Thr Leu
145                 150                 155                 160

Ala Ala Tyr Arg Pro Glu Ala Thr Leu Gly Val Glu Val Ser Asp Ser
                165                 170                 175

Ser Val Asn Cys Ile Glu Gln Thr Thr Glu Trp Thr Ala Cys Ser Lys
            180                 185                 190

Ser Cys Gly Met Gly Phe Ser Thr Arg Val Thr Asn Arg Asn Arg Gln
        195                 200                 205

Cys Glu Met Leu Lys Gln Thr Arg Leu Cys Met Val Arg Pro Cys Glu
    210                 215                 220

Gln Glu Pro Glu Gln Pro Thr Asp Lys Lys Gly Lys Lys Cys Leu Arg
225                 230                 235                 240

Thr Lys Lys Ser Leu Lys Ala Ile His Leu Gln Phe Lys Asn Cys Thr
                245                 250                 255

Ser Leu His Thr Tyr Lys Pro Arg Phe Cys Gly Val Cys Ser Asp Gly
            260                 265                 270

Arg Cys Cys Thr Pro His Asn Thr Lys Thr Ile Gln Ala Glu Phe Gln
        275                 280                 285

Cys Ser Pro Gly Gln Ile Val Lys Lys Pro Val Met Val Ile Gly Thr

-continued

```
    290                 295                 300

Cys Thr Cys His Thr Asn Cys Pro Lys Asn Asn Glu Ala Phe Leu Gln
305                 310                 315                 320

Glu Leu Glu Leu Lys Thr Thr Arg Gly Lys Met
                325                 330
```